United States Patent
Mederski et al.

(10) Patent No.: US 7,557,102 B2
(45) Date of Patent: Jul. 7, 2009

(54) PYRAZOLIDINE-1,2-DICARBOXYLDIPHE-NYLAMIDE DERIVATIVES AS COAGULATION FACTOR XA INHIBITORS FOR THE TREATMENT OF THROMBOSES

(75) Inventors: Werner Mederski, Zwingenberg (DE); Christos Tsaklakidis, Weinheim (DE); Dieter Dorsch, Ober-Ramstadt (DE); Bertram Cezanne, Mörfelden-Walldorf (DE); Johannes Gleitz, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 569 days.

(21) Appl. No.: 10/551,559

(22) PCT Filed: Mar. 9, 2004

(86) PCT No.: PCT/EP2004/002407

§ 371 (c)(1), (2), (4) Date: Oct. 3, 2005

(87) PCT Pub. No.: WO2004/087696

PCT Pub. Date: Oct. 14, 2004

(65) Prior Publication Data

US 2006/0183742 A1    Aug. 17, 2006

(30) Foreign Application Priority Data

Apr. 3, 2003 (DE) ................. 103 15 377
Jun. 30, 2003 (DE) ................. 103 29 295
Aug. 8, 2003 (DE) ................. 103 36 570

(51) Int. Cl.
- *A61K 31/5377* (2006.01)
- *A61K 31/497* (2006.01)
- *A61K 31/454* (2006.01)
- *A61K 31/4439* (2006.01)
- *C07D 413/02* (2006.01)

(52) U.S. Cl. ............. 514/235.5; 514/326; 514/341; 514/397; 514/406; 544/140; 544/405; 546/211; 546/275.4; 548/311.1; 548/356.1

(58) Field of Classification Search ............ None
See application file for complete search history.

(56) References Cited

U.S. PATENT DOCUMENTS

2002/0002183 A1   1/2002   Zhu et al.

2003/0105084 A1   6/2003   Clark et al.
2004/0097550 A1   5/2004   Mederski et al.

FOREIGN PATENT DOCUMENTS

| WO | WO 0164642  | 9/2001 |
| WO | WO 02074735 | 9/2002 |
| WO | WO 03024971 | 3/2003 |

OTHER PUBLICATIONS

Database Medline 'Online! US National Libraray of Medicine (NLM), Bethesda, MD, US; 1972 Roubal Z et al: "Newly Synthesized Pyrazolidine Derivatives as Potential Activators of Fibrinolysis and Antiaggregating Agents." Database Accession No. NLM4669826 XP002283716.

Database Medline'Online! US National Library of Medicine (NLM), Bethesda, MD, US; 1972 Muratova J et al: "Effect of Pyrazolidine Derivatives on Experimental Venous Thrombosis in Rabbitis." Database Accession No. NLM4273931 XP002283717.

Database Caplus 'Online! Chemical Abstracts Service, Columbus, Ohio, US; 1994 Vainiotalo, P. et al: "N, N-Coupled Heterobicycles From Cyclic Hydrazine Derivatives. Part 6. Electron Ioniaztion Mass Spectrometry of Some Substituted 1-Thiocarbamoyl and 1-Carbamoylpyrazlidines" Retrieved From STN Database Accession No. 1994:190889 XP002283718.

Database Caplus 'Online! Chemical Abstracts Service, Columbus, HIO, US; 1973 Zinner, G. et al: "Carbamoylation of Hydrazine Derivatives" Retrieved From STN Database Accession No. 1973:97543 XP002283719.

Database Caplus 'Onoine! Chemical Abstracts Service, Columbus Ohio, US; 1972 Bollbuck, Guenter et al: "Reactions of 4-Aryl Semicarbazides" Retrieved From STN Database Accession No. 1972:59168 XP002283720.

*Primary Examiner*—Kamal A Saeed
(74) *Attorney, Agent, or Firm*—Millen. White, Zelano, Branigan, P.C.

(57) ABSTRACT

Novel compounds of the formula (I), in which R, $R^1$, $R^2$ and $R^3$ have the meanings indicated in Patent Claim 1, are inhibitors of coagulation factor Xa and can be employed for the prophylaxis and/or therapy of thromboembolic diseases and for the treatment of tumors.

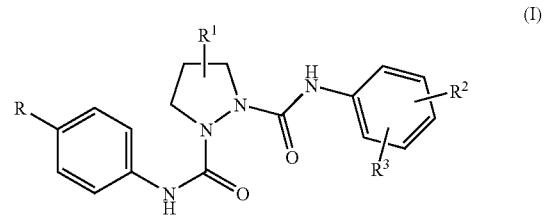

(I)

14 Claims, No Drawings

PYRAZOLIDINE-1,2-DICARBOXYLDIPHENYLAMIDE DERIVATIVES AS COAGULATION FACTOR XA INHIBITORS FOR THE TREATMENT OF THROMBOSES

The invention relates to compounds of the formula I

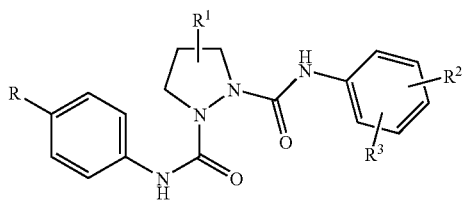

in which
R denotes H, A, A—CO—, Hal, —C≡C—H, —C≡C—A or —C≡C—C(=O)—A,
$R^1$ denotes H, =O, Hal, A, OH, OA, A—COO—, Ph—$(CH_2)_n$—COO—, cycloalkyl-$(CH_2)_n$—COO—, A—CONH—, A—CONA—, Ph—CONA—, $N_3$, $NH_2$, $NO_2$, CN, COOH, COOA, $CONH_2$, CONHA, $CON(A)_2$, O-allyl, O-propargyl, O-benzyl, =N—OH, =N—OA or =$CF_2$,
Ph denotes phenyl which is unsubstituted or mono-, di- or trisubstituted by A, OA or Hal,
$R^2$ denotes H, Hal or A,
$R^3$ denotes a monocyclic saturated, unsaturated or aromatic heterocycle having 1 to 4 N, O and/or S atoms, which may be unsubstituted or mono-, di- or trisubstituted by Hal, A, OA, CN, $(CH_2)_n$OH, $(CH_2)_n$Hal, $NR^4R^5$, =NH, =N—OH, =N—OA and/or carbonyl oxygen (=O), or $CONR^4R^5$,
$R^4$, $R^5$, independently of one another, denote H or A,
$R^4$ and $R^5$ together also denote an alkylene chain having 3, 4 or 5 C atoms, which may also be substituted by A, Hal, OA and/or carbonyl oxygen (=CO),
A denotes unbranched, branched or cyclic alkyl having 1-10 C atoms, in which 1-7 H atoms may also be replaced by F and/or chlorine,
Hal denotes F, Cl, Br or I,
n denotes 0, 1, 2, 3 or 4,
and pharmaceutically usable derivatives, salts, solvates and stereoisomers thereof, including mixtures thereof in all ratios.

The invention had the object of finding novel compounds having valuable properties, in particular those which can be used for the preparation of medicaments.

It has been found that the compounds of the formula I and salts thereof have very valuable pharmacological properties and are well tolerated. In particular, they exhibit factor Xa-inhibiting properties and can therefore be employed for combating and preventing thromboembolic diseases, such as thrombosis, myocardial infarction, arteriosclerosis, inflammation, apoplexy, angina pectoris, restenosis after angioplasty and claudicatio intermittens.

The compounds of the formula I according to the invention may furthermore be inhibitors of the coagulation factors factor VIIa, factor IXa and thrombin in the blood coagulation cascade.

Aromatic amidine derivatives having an antithrombotic action are disclosed, for example, in EP 0 540 051 B1, WO 98/28269, WO 00/71508, WO 00/71511, WO 00/71493, WO 00/71507, WO 00/71509, WO 00/71512, WO 00/71515 or WO 00/71516. Cyclic guanidines for the treatment of thromboembolic diseases are described, for example, in WO 97/08165. Aromatic heterocyclic compounds having a factor Xa inhibitory activity are disclosed, for example, in WO 96/10022. Substituted N-[(aminoiminomethyl)phenylalkyl]azaheterocyclylamides as factor Xa inhibitors are described in WO 96/40679.

Other carboxamide derivatives are known from WO 02/48099 and WO 02/57236, other pyrrolidine derivatives are described in WO 02/100830.

Further heterocyclic derivatives are known from WO 03/045912.

The antithrombotic and anticoagulant effect of the compounds according to the invention is attributed to the inhibitory action against activated coagulation protease, known by the name factor Xa, or to the inhibition of other activated serine proteases, such as factor VIIa, factor IXa or thrombin.

Factor Xa is one of the proteases involved in the complex process of blood coagulation. Factor Xa catalyses the conversion of prothrombin into thrombin. Thrombin cleaves fibrinogen into fibrin monomers, which, after cross-linking, make an elementary contribution to thrombus formation. Activation of thrombin may result in the occurrence of thromboembolic diseases. However, inhibition of thrombin may inhibit the fibrin formation involved in thrombus formation.

The inhibition of thrombin can be measured, for example by the method of G. F. Cousins et al. in *Circulation* 1996, 94, 1705-1712.

Inhibition of factor Xa can thus prevent the formation of thrombin. The compounds of the formula I according to the invention and salts thereof engage in the blood coagulation process by inhibiting factor Xa and thus inhibit the formation of thrombuses.

The inhibition of factor Xa by the compounds according to the invention and the measurement of the anticoagulant and antithrombotic activity can be determined by conventional in-vitro or in-vivo methods. A suitable method is described, for example, by J. Hauptmann et al. in *Thrombosis and Haemostasis* 1990, 63, 220-223.

The inhibition of factor Xa can be measured, for example by the method of T. Hara et al. in *Thromb. Haemostas.* 1994, 71, 314-319.

Coagulation factor VIIa initiates the extrinsic part of the coagulation cascade after binding to tissue factor and contributes to the activation of factor X to give factor Xa. Inhibition of factor VIIa thus prevents the formation of factor Xa and thus subsequent thrombin formation.

The inhibition of factor VIIa by the compounds according to the invention and the measurement of the anticoagulant and antithrombotic activity can be determined by conventional in-vitro or in-vivo methods. A conventional method for the measurement of the inhibition of factor VIIa is described, for example, by H. F. Ronning et al. in *Thrombosis Research* 1996, 84, 73-81.

Coagulation factor IXa is generated in the intrinsic coagulation cascade and is likewise involved in the activation of factor X to give factor Xa. Inhibition of factor IXa can therefore prevent the formation of factor Xa in a different way.

The inhibition of factor IXa by the compounds according to the invention and the measurement of the anticoagulant and antithrombotic activity can be determined by conventional in-vitro or in-vivo methods. A suitable method is described, for example, by J. Chang et al. in *Journal of Biological Chemistry* 1998, 273, 12089-12094.

The compounds according to the invention may furthermore be used for the treatment of tumours, tumour diseases and/or tumour metastases. A correlation between tissue factor TF/factor VIIa and the development of various types of cancer has been indicated by T. Taniguchi and N. R. Lemoine in Biomed. Health Res., (2000), 41 (Molecular Pathogenesis of Pancreatic Cancer), 57-59.

The publications listed below describe an antitumoural action of TF-VII and factor Xa inhibitors in various types of tumour:

K. M. Donnelly et al. in Thromb. Haemost. 1998; 79: 1041-1047;
E. G. Fischer et al. in J. Clin. Invest. 104: 1213-1221 (1999);
B. M. Mueller et al. in J. Clin. Invest. 101: 1372-1378 (1998);
M. E. Bromberg et al. in Thromb. Haemost. 1999; 82: 88-92

The compounds of the formula I can be employed as medicament active ingredients in human and veterinary medicine, in particular for the treatment and prevention of thromboembolic diseases, such as thrombosis, myocardial infarction, arteriosclerosis, inflammation, apoplexy, angina pectoris, restenosis after angioplasty, claudicatio intermittens, venous thrombosis, pulmonary embolism, arterial thrombosis, myocardial ischaemia, unstable angina and strokes based on thrombosis.

The compounds according to the invention are also employed for the treatment or prophylaxis of atherosclerotic diseases, such as coronary arterial disease, cerebral arterial disease or peripheral arterial disease. The compounds are also employed in combination with other thrombolytic agents in myocardial infarction, furthermore for prophylaxis for reocclusion after thrombolysis, percutaneous transluminal angioplasty (PTCA) and coronary bypass operations.

The compounds according to the invention are furthermore used for the prevention of rethrombosis in microsurgery, furthermore as anticoagulants in connection with artificial organs or in haemodialysis.

The compounds are furthermore used in the cleaning of catheters and medical aids in patients in vivo, or as anticoagulants for the preservation of blood, plasma and other blood products in vitro. The compounds according to the invention are furthermore used for diseases in which blood coagulation makes a crucial contribution toward the course of the disease or represents a source of secondary pathology, such as, for example, in cancer, including metastasis, inflammatory diseases, including arthritis, and diabetes.

The compounds according to the invention are furthermore used for the treatment of migraine (F. Morales-Asin et al., Headache, 40, 2000, 45-47).

In the treatment of the diseases described, the compounds according to the invention are also employed in combination with other thrombolytically active compounds, such as, for example, with the "tissue plasminogen activator" t-PA, modified t-PA, streptokinase or urokinase. The compounds according to the invention are administered either at the same time as or before or after the other substances mentioned.

Particular preference is given to simultaneous administration with aspirin in order to prevent recurrence of the clot formation.

The compounds according to the invention are also used in combination with blood platelet glycoprotein receptor (IIb/IIIa) antagonists, which inhibit blood platelet aggregation.

The invention relates to the compounds of the formula I and salts thereof and to a process for the preparation of compounds of the formula I according to Claims 1-10 and pharmaceutically usable derivatives, solvates and stereoisomers thereof, characterised in that a) a compound of the formula II

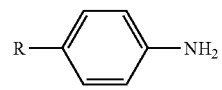

in which R has the meaning indicated in Claim 1, is reacted with a chloroformate derivative to give an intermediate carbamate derivative, which is subsequently reacted with a compound of the formula III-1

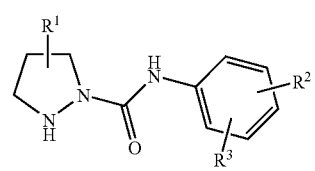

in which $R^1$, $R^2$ and $R^3$ have the meaning indicated in Claim 1, and, if $R^1$ denotes OH, the OH group is optionally in protected form, and subsequently, if desired, the OH-protecting group is removed, or b) a compound of the formula IV

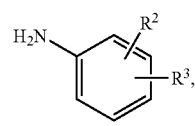

in which $R^2$ and $R^3$ have the meaning indicated in Claim 1, is reacted with a chloroformate derivative to give an intermediate carbamate derivative, which is subsequently reacted with a compound of the formula III-2

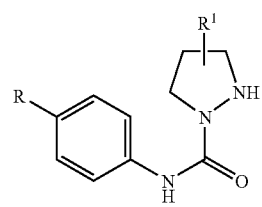

in which R and $R^1$ have the meaning indicated in Claim 1, and, if $R^1$ denotes OH, the OH group is optionally in protected form, and subsequently, if desired, the OH-protecting group is removed, and/or a base or acid of the formula I is converted into one of its salts.

The invention also relates to the optically active forms (stereoisomers), the enantiomers, the racemates, the diastereomers and the hydrates and solvates of these compounds. The term solvates of the compounds is taken to mean adductions of inert solvent molecules onto the compounds which form owing to their mutual attractive force. Solvates are, for example, mono- or dihydrates or alcoholates.

The term pharmaceutically usable derivatives is taken to mean, for example, the salts of the compounds according to the invention and so-called prodrug compounds.

The term prodrug derivatives is taken to mean compounds of the formula I which have been modified with, for example, alkyl or acyl groups, sugars or oligopeptides and which are rapidly cleaved in the organism to form the active compounds according to the invention.

These also include biodegradable polymer derivatives of the compounds according to the invention, as described, for example, in Int. J. Pharm. 115, 61-67 (1995).

The invention also relates to mixtures of the compounds of the formula I according to the invention, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

For all radicals which occur more than once, such as, for example, A, their meanings are independent of one another.

Above and below, the radicals or parameters R, $R^2$ and $R^3$ have the meanings indicated under the formula I, unless expressly stated otherwise.

A denotes alkyl, is unbranched (linear) or branched, and has 1, 2, 3, 4, 5, 6, 7, 8, 9 or 10 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethyl-propyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl.

A very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl. A also denotes cycloalkyl.

Cycloalkyl preferably denotes cyclopropyl, cyclobutyl, cyclopentyl, cyclohexyl or cycloheptyl.

Alkylene preferably denotes methylene, ethylene, propylene, butylene, pentylene or hexylene, furthermore branched alkylene.

R preferably denotes Hal or —C≡C—H.

$R^1$ preferably denotes H, =O, OH, OA, A—COO—, Ph—$(CH_2)_n$—COO— or cycloalkyl-$(CH_2)_n$—COO—, particularly preferably H, =O or OH.

$R^2$ preferably denotes H, Cl, F or alkyl having 1-6 C atoms, such as, for example, methyl, ethyl, propyl, butyl or trifluoromethyl.

$R^3$ preferably denotes a monocyclic saturated, unsaturated or aromatic heterocycle having 1 to 4 N, O and/or S atoms, which may be unsubstituted or mono-, di- or trisubstituted, by Hal, A, OA, =NH and/or carbonyl oxygen (=O), or $R^3$ also denotes $CONR^4R^5$.

$R^3$ particularly preferably denotes 2-oxopiperidin-1-yl, 2-oxopyrrolidin-1-yl, 2-oxo-1H-pyridin-1-yl, 3-oxomorpholin-4-yl, 4-oxo-1H-pyridin-1-yl, 2-oxo-1H-pyrazin-1-yl, 2-oxoimidazolidin-1-yl, 2-iminopiperidin-1-yl, 2-iminopyrrolidin-1-yl, 3-iminomorpholin-4-yl, 2-iminoimidazolidin-1-yl, 2-imino-1H-pyrazin-1-yl, 2,6-dioxopiperidin-1-yl, 2-oxopiperazin-1-yl, 2,6-dioxopiperazin-1-yl, 2,5-dioxopyrrolidin-1-yl, 2-oxo-1,3-oxazolidin-3-yl, 3-oxo-2H-pyridazin-2-yl, 2-caprolactam-1-yl (=2-oxoazepan-1-yl), 2-azabicyclo[2.2.2]octan-3-on-2-yl, 5,6-dihydro-1H-pyrimidin-2-oxo-1-yl, 2-oxo-1,3-oxazinan-3-yl, 4H-1,4-oxazin-4-yl, furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, optionally mono- or disubstituted by Hal and/or A, or $CONR^4R^5$.

In a further embodiment, $R^3$ preferably denotes 2-oxopiperidin-1-yl, 2-oxo-pyrrolidin-1-yl, 2-oxo-1H-pyridin-1-yl, 3-oxomorpholin-4-yl, 4-oxo-1H-pyridin-1-yl, 2-oxo-1H-pyrazin-1-yl, 2-oxoimidazolidin-1-yl, 2-iminopiperidin-1-yl, 2-iminopyrrolidin-1-yl, 3-iminomorpholin-4-yl, 2-iminoimidazolidin-1-yl, 2-imino-1H-pyrazin-1-yl, 2,6-dioxopiperidin-1-yl, 2-oxopiperazin-1-yl, 2,6-dioxopiperazin-1-yl, 2,5-dioxopyrrolidin-1-yl, 2-oxo-1,3-oxazolidin-3-yl, 3-oxo-2H-pyridazin-2-yl, 2-caprolactam-1-yl (=2-oxoazepan-1-yl), 2-aza-bicyclo[2.2.2]octan-3-on-2-yl, 5,6-dihydro-1H-pyrimidin-2-oxo-1-yl, 2-oxo-1,3-oxazinan-3-yl, 4H-1,4-oxazin-4-yl, optionally mono- or disubstituted by Hal and/or A.

$R^3$ very particularly preferably denotes 2-oxopiperidin-1-yl, 2-oxopyrrolidin-1-yl, 2-oxo-1H-pyridin-1-yl, 3-oxomorpholin-4-yl, 4-oxo-1H-pyridin-1-yl, 2-oxo-1H-pyrazin-1-yl, 2-oxoimidazolidin-1-yl, 2,6-dioxopiperidin1-yl, 2-oxo-piperazin-1-yl, 2,6-dioxopiperazin-1-yl, 2,5-dioxopyrrolidin-1-yl, 2-oxo-1,3-oxazolidin-3-yl, 3-oxo-2H-pyridazin-2-yl, 2-caprolactam-1-yl (=2-oxo-azepan-1-yl), 2-azabicyclo[2.2.2]-octan-3-on-2-yl, 5,6-dihydro-1H-pyrimidin-2-oxo-1-yl, 2-oxo-1,3-oxazinan-3-yl or 4H-1,4-oxazin-4-yl.

In $CONR^4R^5$, $NR^4R^5$ preferably denotes methylamino, dimethylamino, ethylamino, diethylamino, pyrrolidino or piperidino.

The compounds of the formula I can have one or more centres of chirality and can therefore occur in various stereoisomeric forms. The formula I encompasses all these forms.

Accordingly, the invention relates, in particular, to the compounds of the formula I in which at least one of the said radicals has one of the preferred meanings indicated above. Some preferred groups of compounds can be expressed by the following sub-formulae Ia to Ih, which conform to the formula I and in which the radicals not designated in greater detail have the meaning indicated under the formula I, but in which in Ia R denotes Hal or —C≡C—H;

in Ib $R^3$ denotes a monocyclic saturated, unsaturated or aromatic heterocycle having 1 to 4 N, O and/or S atoms, which may be unsubstituted or mono-, di- or trisubstituted by Hal, A, OA, =NH and/or carbonyl oxygen (=O), or $CONR^4R^5$ $R^4$, $R^5$, independently of one another, denote H or A, $R^4$ and $R^5$ together also denote an alkylene chain having 3, 4 or 5 C atoms;

in Ic $R^3$ denotes 2-oxopiperidin-1-yl, 2-oxopyrrolidin-1-yl, 2-oxo-1H-pyridin-1-yl, 3-oxomorpholin-4-yl, 4-oxo-1H-pyridin-1-yl, 2-oxo-1H-pyrazin-1-yl, 2-oxoimidazolidin-1-yl, 2-iminopiperidin-1-yl, 2-iminopyrrolidin-1-yl, 3-iminomorpholin-4-yl, 2-iminoimidazolidin-1-yl, 2-imino-1H-pyrazin-1-yl, 2,6-dioxopiperidin1-yl, 2-oxopiperazin-1-yl, 2,6-dioxopiperazin-1-yl, 2,5-dioxo-pyrrolidin-1-yl, 2-oxo-1,3-oxazolidin-3-yl, 3-oxo-2H-pyridazin-2-yl, 2-caprolactam-1-yl (=2-oxoazepan-1-yl), 2-azabicyclo[2.2.2]-octan-3-on-2-yl, 5,6-dihydro-1H-pyrimidin-2-oxo-1-yl, 2-oxo-1,3-oxazinan-3-yl, 4H-1,4-oxazin-4-yl, furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl or pyrazinyl,
optionally mono- or disubstituted by Hal and/or A, or $CONR^4R^5$,
$R^4$, $R^5$, independently of one another, denote H or A,
$R^4$ and $R^5$ together also denote an alkylene chain having 3, 4 or 5 C atoms;

in Id $R^1$ denotes H, =O, OH, OA, A—COO—, Ph—$(CH_2)_n$—COO—, cycloalkyl-$(CH_2)_n$—COO—,
Ph denotes unsubstituted phenyl;

in Ie R denotes Hal or —C≡C—H,
$R^1$ denotes H, =O, OH, OA, A—COO—, Ph—$(CH_2)_n$—COO—, cycloalkyl-$(CH_2)_n$—COO—,
Ph denotes unsubstituted phenyl,
$R^2$ denotes H, Hal or A,
$R^3$ denotes 2-oxopiperidin-1-yl, 2-oxopyrrolidin-1-yl, 2-oxo-1H-pyridin-1-yl, 3-oxomorpholin-4-yl, 4-oxo-1H-pyridin-1-yl, 2-oxo-1H-pyrazin-1-yl, 2-oxoimidazolidin-1-yl, 2-iminopiperidin-1-yl, 2-iminopyrrolidin-1-yl, 3-iminomorpholin-4-yl, 2-iminoimidazolidin-1-yl, 2-imino-1H-pyrazin-1-yl, 2,6-dioxopiperidin1-yl, 2-oxopiperazin-1-yl, 2,6-dioxopiperazin-1-yl, 2,5-dioxo-pyrrolidin-1-yl, 2-oxo-1,3-oxazolidin-3-yl, 3-oxo-2H-pyridazin-2-yl, 2-caprolactam-1-yl (=2-oxoazepan-1-yl), 2-azabicyclo[2.2.2]-octan-3-on-2-yl, 5,6-dihydro-1H-pyrimidin-2-oxo-1-yl, 2-oxo-1,3-oxazinan-3-yl, 4H-1,4-oxazin-4-yl, furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl or pyrazinyl,
optionally mono- or disubstituted by Hal and/or A, or $CONR^4R^5$,
$R^4$, $R^5$, independently of one another, denote H or A,
$R^4$ and $R^5$ together also denote an alkylene chain having 3, 4 or 5 C atoms;

in If $R^3$ denotes 2-oxopiperidin-1-yl, 2-oxopyrrolidin-1-yl, 2-oxo-1H-pyridin-1-yl, 3-oxomorpholin-4-yl, 4-oxo-1H-pyridin-1-yl, 2-oxo-1H-pyrazin-1-yl, 2-oxoimidazolidin-1-yl, 2-iminopiperidin-1-yl, 2-iminopyrrolidin-1-yl, 3-iminomorpholin-4-yl, 2-iminoimidazolidin-1-yl, 2-imino-1H-pyrazin-1-yl, 2,6-dioxopiperidin1-yl, 2-oxopiperazin-1-yl, 2,6-dioxopiperazin-1-yl, 2,5-dioxo-pyrrolidin-1-yl, 2-oxo-1,3-oxazolidin-3-yl, 3-oxo-2H-pyridazin-2-yl, 2-caprolactam-1-yl (=2-oxoazepan-1-yl), 2-azabicyclo[2.2.2]-octan-3-on-2-yl, 5,6-dihydro-1H-pyrimidin-2-oxo-1-yl, 2-oxo-1,3-oxazinan-3-yl or 4H-1,4-oxazin-4-yl,
optionally mono- or disubstituted by Hal and/or A;

in Ig $R^3$ denotes 2-oxopiperidin-1-yl, 2-oxopyrrolidin-1-yl, 2-oxo-1H-pyridin-1-yl, 3-oxomorpholin-4-yl, 4-oxo-1H-pyridin-1-yl, 2-oxo-1H-pyrazin-1-yl, 2-oxoimidazolidin-1-yl, 2,6-dioxopiperidin1-yl, 2-oxopiperazin-1-yl, 2,6-dioxopiperazin-1-yl, 2,5-dioxopyrrolidin-1-yl, 2-oxo-1,3-oxazolidin-3-yl, 3-oxo-2H-pyridazin-2-yl, 2-caprolactam-1-yl (=2-oxoazepan-1-yl), 2-azabicyclo[2.2.2]-octan-3-on-2-yl, 5,6-dihydro-1H-pyrimidin-2-oxo-1-yl, 2-oxo-1, 3-oxazinan-3-yl or 4H-1,4-oxazin-4-yl;

in Ih R denotes Hal or —C≡C—H,
$R^1$ denotes H, =O, OH, OA, A—COO—, Ph—$(CH_2)_n$—COO—, cycloalkyl-$(CH_2)_n$—COO—,
Ph denotes unsubstituted phenyl,
$R^2$ denotes H, Hal or A,
$R^3$ denotes 2-oxopiperidin-1-yl, 2-oxopyrrolidin-1-yl, 2-oxo-1H-pyridin-1-yl, 3-oxomorpholin-4-yl, 4-oxo-1H-pyridin-1-yl, 2-oxo-1H-pyrazin-1-yl, 2-oxoimidazolidin-1-yl, 2,6-dioxopiperidin1-yl, 2-oxopiperazin-1-yl, 2,6-dioxopiperazin-1-yl, 2,5-dioxopyrrolidin-1-yl, 2-oxo-1,3-oxazolidin-3-yl, 3-oxo-2H-pyridazin-2-yl, 2-caprolactam-1-yl (=2-oxoazepan-1-yl), 2-azabicyclo[2.2.2]-octan-3-on-2-yl, 5,6-dihydro-1H-pyrimidin-2-oxo-1-yl, 2-oxo-1,3-oxazinan-3-yl or 4H-1,4-oxazin-4-yl,
A denotes unbranched, branched or cyclic alkyl having 1-10 C atoms, in which 1-7 H atoms may also be replaced by F and/or chlorine,
Hal denotes F, Cl, Br or I,
n denotes 0, 1, 2, 3 or 4, and pharmaceutically usable derivatives, salts, solvates and stereoisomers thereof, including mixtures thereof in all ratios.

The compounds of the formula I and also the starting materials for the preparation thereof are, in addition, prepared by methods known per se, as described in the literature (for example in the standard works, such as Houben-Weyl, Methoden der organischen-Chemie [Methods of Organic Chemistry], Georg-Thieme-Verlag, Stuttgart), to be precise under reaction conditions which are known and suitable for the said reactions. Use can also be made here of variants which are known per se, but are not mentioned here in greater detail.

If desired, the starting materials can also be formed in situ so that they are not isolated from the reaction mixture, but instead are immediately converted further into the compounds of the formula I.

Some of the starting compounds of the formulae II, III-1, III-2 and IV are novel.

Compounds of the formula I can preferably be obtained by reacting compounds of the formula II or IV with a chloroformate derivative, for example 4-nitrophenyl chloroformate, to give an intermediate carbamate and subsequently reacting with compounds of the formula III-1 or III-2.

The reaction is generally carried out in an inert solvent, in the presence of an acid-binding agent, preferably an alkali or alkaline earth metal hydroxide, carbonate or bicarbonate or another salt of a weak acid of the alkali or alkaline earth metals, preferably of potassium, sodium, calcium or caesium. It may also be favourable to add an organic base, such as triethylamine, dimethylaniline, pyridine or quinoline, or an excess of the phenol component of the formula II or of the alkylation derivative of the formula III. Depending on the conditions used, the reaction time is between a few minutes and 14 days, the reaction temperature is between about 0° and 150°, normally between 20° and 130°.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Compounds of the formula I can furthermore be obtained by removing the protecting group from compounds of the formula I which contain an OH— or NH-protecting group.

Preferred starting materials for the protecting group removal are those which conform to the formula I, but contain corresponding protected amino and/or hydroxyl groups instead of one or more free amino and/or hydroxyl groups, preferably those which carry an amino-protecting group instead of an H atom bonded to an N atom, in particular those which carry an R'—N group, in which R' denotes an amino-protecting group, instead of an HN group, and/or those which carry a hydroxyl-protecting group instead of the H atom of a hydroxyl group, for example those which conform to the formula I, but carry an —OR" or —COOR" group, in which R" denotes a hydroxyl-protecting group, instead of an —OH or —COOH group.

It is also possible for a plurality of—identical or different—protected amino and/or hydroxyl groups to be present in the molecule of the starting material. If the protecting groups present are different from one another, they can in many cases be removed selectively.

The term "amino-protecting group" is known in general terms and relates to groups which are suitable for protecting (blocking) an amino group against chemical reactions, but which are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size is furthermore not crucial; however, preference is given to those having 1-20, in particular 1-8, C atoms. The term "acyl group" is to be understood in the broadest sense in connection with the present process. It encompasses acyl groups derived from aliphatic, araliphatic, aromatic or heterocyclic carboxylic acids or sulfonic acids, and, in particular, alkoxycarbonyl, aryloxycarbonyl and especially aralkoxycarbonyl groups. Examples of such acyl groups are alkanoyl, such as acetyl, propionyl, butyryl; aralkanoyl, such as phenylacetyl; aroyl, such as benzoyl or tolyl; aryloxyalkanoyl, such as POA; alkoxycarbonyl, such as methoxycarbonyl, ethoxycarbonyl, 2,2,2-trichloroethoxycarbonyl, BOC (tert-butoxycarbonyl), 2-iodoethoxycarbonyl; aralkoxycarbonyl, such as CBZ ("carbobenzoxy"), 4-methoxybenzyloxycarbonyl, FMOC; arylsulfonyl, such as Mtr. Preferred amino-protecting groups are BOC and Mtr, furthermore CBZ, Fmoc, benzyl and acetyl.

The term "hydroxyl-protecting group" is likewise known in general terms and relates to groups which are suitable for protecting a hydroxyl group against chemical reactions, but which are easy to remove after the desired chemical reaction has been carried out elsewhere in the molecule. Typical of such groups are the above-mentioned unsubstituted or substituted aryl, aralkyl or acyl groups, furthermore also alkyl groups or alkylsilyl protecting groups. The nature and size of the hydroxyl-protecting groups are not crucial since they are removed again after the desired chemical reaction or reaction sequence; preference is given to groups having 1-20, in particular 1-10, C atoms. Examples of hydroxyl-protecting groups are, inter alia, benzyl, 4-methoxybenzyl, p-nitrobenzoyl, p-toluenesulfonyl, tert-butyl and acetyl, where benzyl and tert-butyl are particularly preferred. If $R^1$ denotes OH, very particular preference is given to the tert-butyldimethylsilyl protecting group.

The compounds of the formula I are liberated from their functional derivatives—depending on the protecting group used—for example using strong acids, advantageously using TFA or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane; furthermore also alcohols, such as methanol, ethanol or isopropanol, and water. Mixtures of the above-mentioned solvents are furthermore suitable. TFA is preferably used in excess without addition of a further solvent, perchloric acid is preferably used in the form of a mixture of acetic acid and 70% perchloric acid in the ratio 9:1. The reaction temperatures for the cleavage are advantageously between about 0 and about 50°, preferably between 15 and 30° (room temperature).

The BOC, OBut and Mtr groups can, for example, preferably be removed using TFA in dichloromethane or using approximately 3 to 5N HCl in dioxane at 15-30°, and the FMOC group can be removed using an approximately 5 to 50% solution of dimethylamine, diethylamine or piperidine in DMF at 15-30°.

Alkylsilyl protecting groups, such as, for example, the tert-butyldimethylsilyl protecting group, are removed, for example, using tetra-n-butylammonium fluoride.

Protecting groups which can be removed hydrogenolytically (for example CBZ, benzyl or the liberation of the amidino group from its oxadiazole derivative)) can be removed, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° and pressures between about 1 and 200 bar, preferably at 20-30° and 1-10 bar. Hydrogenolysis of the CBZ group succeeds well, for example, on 5 to 10% Pd/C in methanol or using ammonium formate (instead of hydrogen) on Pd/C in methanol/DMF at 20-30°.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, trifluoromethylbenzene, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide, N-methylpyrrolidone (NMP) or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Esters can be saponified, for example, using acetic acid or using NaOH or KOH in water, water/THF or water/dioxane, at temperatures between 0 and 100°.

Free amino groups can furthermore be acylated in a conventional manner using an acid chloride or anhydride or alkylated using an unsubstituted or substituted alkyl halide or reacted with $CH_3$—$C(=NH)$—OEt, advantageously in an inert solvent, such as dichloromethane or THF and/or in the presence of a base, such as triethylamine or pyridine, at temperatures between −60 and +30°.

A base of the formula I can be converted into the associated acid-addition salt using an acid, for example by reaction of equivalent amounts of the base and the acid in an inert solvent, such as ethanol, followed by evaporation. Suitable acids for this reaction are, in particular, those which give physiologically acceptable salts. Thus, it is possible to use inorganic acids, for example sulfuric acid, nitric acid, hydrohalic acids, such as hydrochloric acid or hydrobromic acid, phosphoric acids, such as orthophosphoric acid, sulfamic acid, furthermore organic acids, in particular aliphatic, alicyclic, araliphatic, aromatic or heterocyclic mono- or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids, laurylsulfuric acid. Salts with physiologically unacceptable acids, for example picrates, can be used for the isolation and/or purification of the compounds of the formula I.

On the other hand, compounds of the formula I can be converted into the corresponding metal salts, in particular alkali metal or alkaline earth metal salts, or into the corresponding ammonium salts using bases (for example sodium hydroxide, potassium hydroxide, sodium carbonate or potassium carbonate).

It is also possible to use physiologically acceptable organic bases, such as, for example, ethanolamine.

The preferred meanings of the radicals in the compounds of the formula III-1, III-2 and VI mentioned below correspond to those as mentioned above for the compounds of the formula I, unless expressly stated otherwise.

The invention also relates to the intermediate compounds of the formula III-1

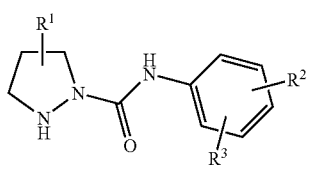

III-1 in which $R^1$ denotes H, =O, Hal, A, $OR^6$, OA, A—COO—, Ph—$(CH_2)_n$—COO—, cycloalkyl-$(CH_2)_n$—COO—, A—CONH—, A—CONA—, Ph—CONA—, $N_3$, $NH_2$, $NO_2$, CN, COOH, COOA, $CONH_2$, CONHA, $CON(A)_2$, O-allyl, O-propargyl, O-benzyl, =N—OH, =N—OA, or =$CF_2$, Ph denotes phenyl which is unsubstituted or mono-, di- or trisubstituted by A, OA or Hal, $R^2$ denotes H, Hal or A, $R^3$ denotes a monocyclic saturated, unsaturated or aromatic heterocycle having 1 to 4 N, O and/or S atoms, which may be unsubstituted or mono-, di- or trisubstituted by Hal, A, OA, CN, $(CH_2)_n$OH, $(CH_2)_n$Hal, $NR^4R^5$, =NH, =N—OH, =N—OA, and/or carbonyl oxygen (=O), $CONR^4R^5$, $R^4$, $R^5$, independently of one another, denote H or A, $R^4$ and $R^5$ together also denote an alkylene chain having 3, 4 or 5 C atoms, which may also be substituted by A, Hal, OA and/or carbonyl oxygen (=CO), $R^6$ denotes an OH-protecting group, A denotes unbranched, branched or cyclic alkyl having 1-10 C atoms, in which 1-7 H atoms may also be replaced by F and/or chlorine, Hal denotes F, Cl, Br or I, n denotes 0, 1, 2, 3 or 4, and isomers and salts thereof.

The invention preferably relates to the intermediate compounds of the formula III-1, in which $R^1$ denotes H, =O, $OR^6$, OA, A—COO—, Ph—$(CH_2)_n$—COO— or cycloalkyl-$(CH_2)_n$—COO—, Ph denotes unsubstituted phenyl, $R^2$ denotes H, Hal or A, $R^3$ denotes 2-oxopiperidin-1-yl, 2-oxopyrrolidin-1-yl, 2-oxo-1H-pyridin-1-yl, 3-oxomorpholin-4-yl, 4-oxo-1H-pyridin-1-yl, 2-oxo-1H-pyrazin-1-yl, 2-oxoimidazolidin-1-yl, 2,6-dioxo-piperidin-1-yl, 2-oxopiperazin-1-yl, 2,6-dioxopiperazin-1-yl, 2,5-dioxopyrrolidin-1-yl, 2-oxo-1,3-oxazolidin-3-yl, 3-oxo-2H-pyridazin-2-yl, 2-caprolactam-1-yl (=2-oxoazepan-1-yl), 2-azabicyclo[2.2.2]-octan-3-on-2-yl, 5,6-dihydro-1H-pyrimidin-2-oxo-1-yl, 2-oxo-1,3-oxazinan-3-yl or 4H-1,4-oxazin-4-yl, $R^6$ denotes an OH-protecting group, A denotes unbranched, branched or cyclic alkyl having 1-10 C atoms, in which 1-7 H atoms may also be replaced by F and/or chlorine, Hal denotes F, Cl, Br or I, n denotes 0, 1, 2, 3 or 4, and isomers and salts thereof.

The invention particularly preferably relates to the intermediate compounds of the formula III-1, in which $R^1$ denotes H, =O or $OR^6$, $R^2$ denotes H, Hal or A, $R^3$ denotes 2-oxopiperidin-1-yl, 2-oxopyrrolidin-1-yl, 2-oxo-1H-pyridin-1-yl, 3-oxomorpholin-4-yl, 4-oxo-1H-pyridin-1-yl, 2-oxo-1H-pyrazin-1-yl, 2-oxoimidazolidin-1-yl, 2,6-dioxopiperidin1-yl, 2-oxopiperazin-1-yl, 2,6-dioxopiperazin-1-yl, 2,5-dioxopyrrolidin-1-yl, 2-oxo-1,3-oxazolidin-3-yl, 3-oxo-2H-pyridazin-2-yl, 2-caprolactam-1-yl (=2-oxoazepan-1-yl), 2-azabicyclo[2.2.2]-octan-3-on-2-yl, 5,6-dihydro-1H-pyrimidin-2-oxo-1-yl, 2-oxo-1,3-oxazinan-3-yl, 4H-1,4-oxazin-4-yl, $R^6$ denotes an alkylsilyl protecting group, A denotes unbranched, branched or cyclic alkyl having 1-10 C atoms, in which 1-7 H atoms may also be replaced by F and/or chlorine, Hal denotes F, Cl, Br or I, n denotes 0, 1, 2, 3 or 4, and isomers and salts thereof.

The invention also relates to the intermediate compounds of the formula III-2

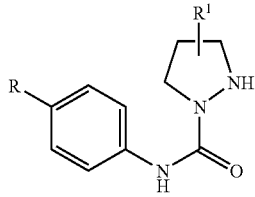

III-2 in which
R denotes H, A, A—CO—, Hal, —C≡C—H, —C≡C—A or —C≡C—C(=O)—A,
$R^1$ denotes H, =O, Hal, A, $OR^6$, OA, A—COO—, Ph—$(CH_2)_n$—COO—, cycloalkyl-$(CH_2)_n$—COO—, A—CONH—, A—CONA—, Ph—CONA—, $N_3$, $NH_2$, $NO_2$, CN, COOH, COOA, $CONH_2$, CONHA, $CON(A)_2$, O-allyl, O-propargyl, O-benzyl, =N—OH, =N—OA or $=CF_2$,
Ph denotes phenyl which is unsubstituted or mono-, di- or trisubstituted by A, OA or Hal,
$R^6$ denotes an OH-protecting group,
A denotes unbranched, branched or cyclic alkyl having 1-10 C atoms, in which 1-7 H atoms may also be replaced by F and/or chlorine,
Hal denotes F, Cl, Br or I,
n denotes 0, 1, 2, 3 or 4,
where, if $R^1$ denotes H, R does not denote Cl,
and isomers and salts thereof.

The invention preferably also relates to the intermediate compounds of the formula III-2, in which
R denotes Hal or —C≡C—H,
$R^1$ denotes H, =O, $OR^6$, OA, A—COO—, Ph—$(CH_2)_n$—COO— or cycloalkyl-$(CH_2)_n$—COO—,
Ph denotes phenyl which is unsubstituted or mono-, di- or trisubstituted by A, OA or Hal,
$R^6$ denotes an OH-protecting group,
A denotes unbranched, branched or cyclic alkyl having 1-10 C atoms, in which 1-7 H atoms may also be replaced by F and/or chlorine,
Hal denotes F, Cl, Br or I,
n denotes 0, 1, 2, 3 or 4,
where, if $R^1$ denotes H, R does not denote Cl,
and isomers and salts thereof.

The invention furthermore particularly preferably relates to the intermediate compounds of the formula III-2, in which
R denotes Hal or —C≡C—H,
$R^1$ denotes H, =O or $OR^6$,
$R^6$ denotes an alkylsilyl protecting group,
Hal denotes F, Cl, Br or I,
where, if $R^1$ denotes H, R does not denote Cl,
and isomers and salts thereof.

The compound N-(4-chlorophenyl)-1-pyrazolidinecarboxamide is described in J. Heterocyclic Chem. (1993), 30(6), 1641-4 and in Pharmazie (1991), 46(6), 418-22.

Precursors for the preparation of the compounds of the formula III-1 or III-2 are the compounds of the formula VI

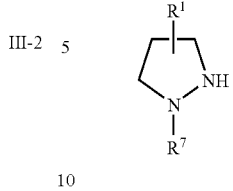

VI in which
$R^1$ has, the meanings indicated under the formulae III-1 and III-2 and
$R^7$ denotes an amino-protecting group.

The amino-protecting group preferably denotes tert-butyloxycarbonyl (BOC) or benzyloxycarbonyl (Z).

The preparation of compounds of the formula VI in which $R^1$ denotes H, for example the pyrazolidine compounds of the formula VI-1 and VI-2, is carried out by a known preparation procedure starting from Z-protected tert-butylcarbazane and 1,3-dibromopropane in 2 steps (Dutta, A. S.; Morley, J. S. *J. Chem. Soc. Perkin Trans* 1 1975, 1712)

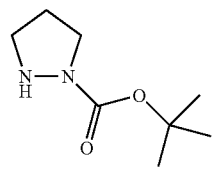

VI-1

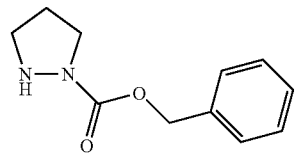

VI-2

Compounds of the formula VI, in which
$R^1$ denotes OH or $OR^6$,
$R^6$ denotes a silyl protecting group,
$R^7$ denotes BOC or Z,
are novel.

The invention therefore also relates to the intermediate compounds of the formula VI

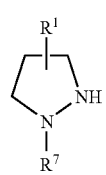

VI in which
$R^1$ denotes OH or $OR^6$,
$R^6$ denotes a silyl protecting group,
$R^7$ denotes tert-butyloxycarbonyl (BOC) or benzyloxycarbonyl (Z),
and isomers thereof.

Particular preference is given to compounds of the formula VI in which $R^6$ denotes tert-butyldimethylsilyl.

The compounds are obtained analogously to the following scheme directly from tert-butylcarbazane and silyl-protected 1,3-dibromopropan-2-ol in one step. The reaction does not succeed with the free OH compound.

Compounds of the formula I according to the invention may be chiral owing to their molecular structure and may accordingly occur in various enantiomeric forms. They can therefore exist in racemic or in optically active form.

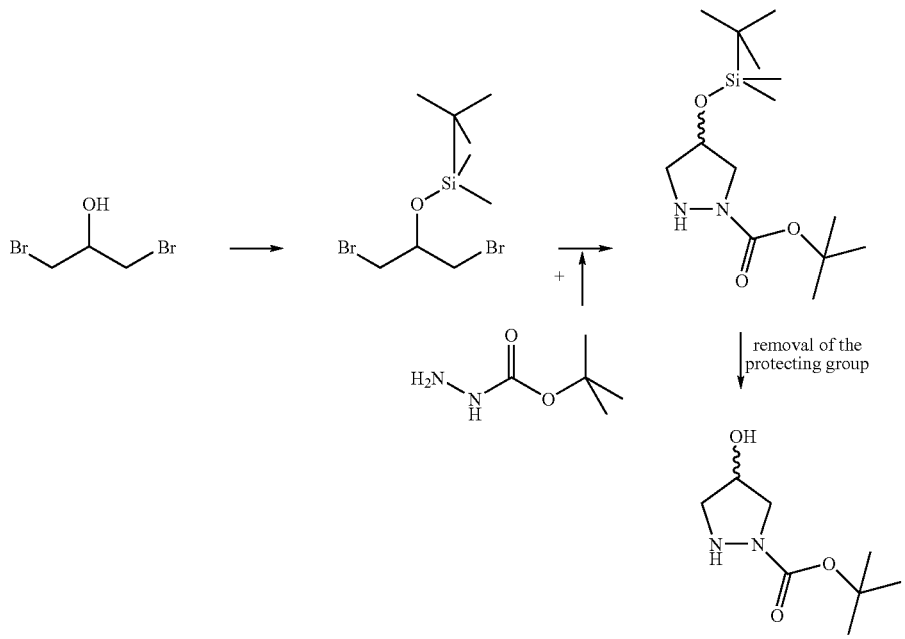

The silyl protecting group is removed, if necessary, by known methods, for example using tetra-n-butylammonium fluoride.

The invention furthermore relates to a process for the preparation of compounds of the formula VI

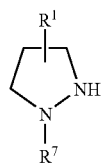

VI in which

R$^1$ denotes OH or OR$^6$,

R$^6$ denotes a silyl protecting group,

R$^7$ denotes tert-butyloxycarbonyl (BOC) or benzyloxycarbonyl (Z), and isomers thereof, obtainable by reaction of a compound of the formula VII

 R$^7$—NHNH$_2$    VII, in which R$^7$ denotes BOC or Z, with silyl-protected 1,3-dibromopropan-2-ol, and optionally subsequent removal of the protecting group.

Particular preference is given to a process for the preparation of compounds of the formula VI in which R$^6$ denotes tert-butyldimethylsilyl.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitably N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

The invention furthermore relates to the use of the compounds of the formula I and/or physiologically acceptable salts thereof for the preparation of a medicament (pharmaceutical composition), in particular by non-chemical methods. They can be converted here into a suitable dosage form together with at least one solid, liquid and/or semi-liquid excipient or adjuvant and, if desired, in combination with one or more further active ingredients.

The invention furthermore relates to medicaments comprising at least one compound of the formula I and/or pharmaceutically usable derivatives, solvates and stereoisomers thereof, including mixtures thereof in all ratios, and optionally excipients and/or adjuvants.

These compositions can be used as medicaments in human or veterinary medicine. Suitable excipients are organic or inorganic substances which are suitable for enteral (for example oral), parenteral or topical administration and do not react with the novel compounds, for example water, vegetable oils, benzyl alcohols, alkylene glycols, polyethylene glycols, glycerol triacetate, gelatine, carbohydrates, such as lactose or starch, magnesium stearate, talc, Vaseline. Suitable for oral administration are, in particular, tablets, pills, coated tablets, capsules, powders, granules, syrups, juices or drops, suitable for rectal administration are suppositories, suitable for parenteral administration are solutions, preferably oil-based or aqueous solutions, furthermore suspensions, emulsions or implants, and suitable for topical application are ointments, creams or, powders or also as nasal spray. The novel compounds may also be lyophilised and the resultant lyophilisates used, for example, to prepare injection preparations. The compositions indicated may be sterilised and/or comprise adjuvants, such as lubricants, preservatives, stabilisers and/or wetting agents, emulsifying agents, salts for modifying the osmotic pressure, buffer substances, colorants, flavours and/or a plurality of further active ingredients, for example one or more vitamins.

The compounds of the formula I and physiologically acceptable salts thereof can be used for combating and preventing thromboembolic diseases, such as thrombosis, myocardial infarction, arteriosclerosis, inflammation, apoplexy, angina pectoris, restenosis after angioplasty, claudicatio intermittens, migraine, tumours, tumour diseases and/or tumour metastases.

In general, the substances according to the invention are preferably administered here in doses between about 1 and 500 mg, in particular between 5 and 100 mg, per dosage unit. The daily dose is preferably between about 0.02 and 10 mg/kg of body weight. However, the specific dose for each patient depends on a very wide variety of factors, for example on the efficacy of the specific compound employed, on the age, body weight, general state of health, sex, on the diet, on the time and method of administration, on the excretion rate, medicament combination and severity of the particular disease to which the therapy applies. Oral administration is preferred.

The invention furthermore relates to medicaments comprising at least one compound of the formula I and/or pharmaceutically usable derivatives, solvates and stereoisomers thereof, including mixtures thereof in all ratios, and at least one further medicament active ingredient.

The invention also relates to a set (kit) consisting of separate packs of (a) an effective amount of a compound of the formula I and/or pharmaceutically usable derivatives, salts, solvates and stereoisomers thereof, including mixtures thereof in all ratios, and (b) an effective amount of a further medicament active ingredient.

The set comprises suitable containers, such as boxes, individual bottles, bags or ampoules. The set may, for example, comprise separate ampoules each containing an effective amount of a compound of the formula I and/or pharmaceutically usable derivatives, salts, solvates and stereoisomers thereof, including mixtures thereof in all ratios, and an effective amount of a further medicament active ingredient in dissolved or lyophilised form.

The invention furthermore relates to the use of compounds of the formula I and/or pharmaceutically usable derivatives, salts, solvates and stereoisomers thereof, including mixtures thereof in all ratios, for the preparation of a medicament for the treatment of thromboses, myocardial infarction, arteriosclerosis, inflammation, apoplexy, angina pectoris, restenosis after angioplasty, claudicatio intermittens, migraine, tumours, tumour diseases and/or tumour metastases, in combination with at least one further medicament active ingredient.

Above and below, all temperatures are indicated in ° C. In the following examples, "conventional work-up" means: water is added if necessary, the pH is adjusted, if necessary, to values between 2 and 10, depending on the constitution of the end product, the mixture is extracted with ethyl acetate or dichloromethane, the phases are separated, the organic phase is dried-over sodium sulfate and evaporated, and the product is purified by chromatography on silica gel and/or by crystallisation. Rf values on silica gel; eluent: ethyl acetate/methanol 9:1.

Mass spectrometry (MS): EI (electron impact ionisation) $M^+$

ESI (electrospray ionisation) $(M+H)^+$ (unless stated otherwise)

EXAMPLE 1

1-N-[(4-Ethynylphenyl)]-2-N-{[3-chloro-4-(3-oxomorpholin-4-yl)phenyl]}-pyrazolidine-1,2-dicarboxamide ("A1")

Step 1 tert-Butyl 2-[3-chloro-4-(3-oxomorpholin-4-yl)phenylcarbamoyl]pyrazolidine-1-carboxylate 340 mg (1.5 mmol) of 4-(4-amino-2-chlorophenyl)morpholin-3-one are dissolved in 10 ml of dichloromethane (DCM), 302 mg (1.5 mmol) of 4-nitrophenyl chloroformate and 121 µl (1.5 mmol) of pyridine are subsequently added successively, and the mixture is stirred at RT for 1 h. 300.0 mg (0.7 mmol) of tert-butyl pyrazolidine-1-carboxylate and 0.765 mg (4.5 mmol) of N-ethyldiisopropylamine are added to this reaction mixture. After stirring at RT for 20 h, the mixture is subjected to conventional work-up, giving 420 mg (57.3%) of step 1; MS (FAB) m/e=425/427 $(M+H)^+$.

Step 2

N-[3-chloro-4-(3-oxomorpholin-4-yl)phenyl]pyrazolidine-1-carboxamide 410 mg (0.84 mmol) of step 1 are dissolved in 5 ml of dioxane, and 5 ml (20 mmol) of 4M HCl in dioxane are added. After stirring at RT for 5 h, the mixture is subjected to conventional work-up, giving 330 mg (Y=91.5%) of step 2. MS (FAB) m/e=325/327 $(M+H)^+$.

Step 3

84.3 mg. (0.7 mmol) of 4-ethynylaniline are dissolved in 10 ml of DCM, 140.7 mg (0.7 mmol) of 4-nitrophenyl chloroformate and 56.4 µl (0.7 mmol) of pyridine are subsequently added successively, and the mixture is stirred at RT for 1 h. 300.0 mg (0.7 mmol) of step 2 and 0.475 ml (2.8 mmol) of N-ethyldiisopropylamine are added to this reaction mixture. After stirring at RT for 20 h, the mixture is subjected to conventional work-up. The residue is recrystallised from EA, giving 170 mg (Y=50.6%) of "A1" as crystals; MS (FAB) m/e=468/470 (M+H)+.

The following compounds are obtained analogously
1-N-[(4-chlorophenyl)]-2-N-{[3-chloro-4-(3-oxomorpholin-4-yl)phenyl]}-pyrazolidine-1,2-dicarboxamide ("A2"), M+H+ 478, 480;
1-N-[(4-chlorophenyl)]-2-N-{[4-(2-oxo-2H-pyridin-1-yl) phenyl]}pyrazolidine-1,2-dicarboxamide, M+H+ 438, 440;
1-N-[(4-chlorophenyl)]-2-N-{[3-methyl-4-(3-oxomorpholin-4-yl)-phenyl]}pyrazolidine-1,2-dicarboxamide, M+H+ 458, 460;
1-N-[(4-chlorophenyl)]-2-N-{[3-fluoro-4-(3-oxomorpholin-4-yl)phenyl]}-pyrazolidine-1,2-dicarboxamide, M+H+ 462, 464;
1-N-[(4-chlorophenyl)]-2-N-{[3-chloro-4-(2-oxo-2H-pyridin-1-yl)-phenyl]}pyrazolidine-1,2-dicarboxamide, M+H+ 472, 474;
1-N-[(4-chlorophenyl)]-2-N-{[3-chloro-4-(2-azabicyclo [2.2.2]-octan-3-on-2-yl)phenyl]}pyrazolidine-1,2-dicarboxamide, M+H+ 502, 504;
1-N-[(4-chlorophenyl)]-2-N-{[3-methyl-4-(2-oxopyrrolidinyl)phenyl]}-pyrazolidine-1,2-dicarboxamide,
1-N-[(4-chlorophenyl)]-2-N-{[4-(3-oxomorpholin-4-yl) phenyl]}-4-oxo-pyrazolidine-1,2-dicarboxamide,
1-N-[(4-chlorophenyl)]-2-N-{[4-(2-oxopiperidinyl)phenyl]} pyrazolidine-1,2-dicarboxamide, M+H+ 442, 444;
1-N-[(4-chlorophenyl)]-2-N-{[4-(3-oxomorpholin-4-yl) phenyl]}pyrazolidine-1,2-dicarboxamide, M+H+ 444, 446;
1-N-[(4-chlorophenyl)]-2-N-{[2-fluoro-4-(3-oxomorpholin-4-yl)phenyl]}-pyrazolidine-1,2-dicarboxamide, M+H+ 462, 464;
1-N-[(4-chlorophenyl)]-2-N-{[3-trifluoromethyl-4-(2-azabicyclo[2.2.2]-octan-3-on-2-yl)phenyl]}pyrazolidine-1,2-dicarboxamide, M+H+ 536, 538;
1-N-[(4-chlorophenyl)]-2-N-{[4-(2-azabicyclo[2.2.2]-octan-3-on-2-yl)-phenyl]}pyrazolidine-1,2-dicarboxamide, M+H+ 468, 470;
1-N-[(4-chlorophenyl)]-2-N-{[4-(2-oxo-1,3-oxazinan-3-yl) phenyl]}-pyrazolidine-1,2-dicarboxamide, M+H+ 444, 446;
1-N-[(4-ethynylphenyl)]-2-N-{[4-(2-oxo-2H-pyridin-1-yl) phenyl]}pyrazolidine-1,2-dicarboxamide,
1-N-[(4-ethynylphenyl)]-2-N-{[3-methyl-4-(3-oxomorpholin-4-yl)-phenyl]}pyrazolidine-1,2-dicarboxamide,
1-N-[(4-bromophenyl)]-2-N-{[4-(2-oxo-2H-pyridin-1-yl) phenyl]}pyrazolidine-1,2-dicarboxamide ("A3"), M+H+ 483.

EXAMPLE 2

1-N-[(4-Chlorophenyl)]-2-N-{[4-(2-oxo-2H-pyridin-1-yl)phenyl]}-4-hydroxy-pyrazolidine-1,2-dicarboxamide ("B1")

Step 1

(2-Bromo-1-bromomethylethoxy)-tert-butyldimethylsilane 26.7 g (122.4 mmol) of 1,3-dibromopropan-2-ol are dissolved in 150 ml of DCM, and 18.35 g (269.59 mmol) of imidazole are added. 18.47 g (122.54 mmol) of tert-butyldimethylchlorosilane in 150 ml of DCM are subsequently added dropwise. The mixture is left to stir at RT for 18 h, subjected to conventional work-up, giving, as crude product, 39.1 g (Y=95.9%) of step 1 as colourless oil, which is employed directly in step 2.

Step 2 tert-Butyl 4-(tert-butyldimethylsilanyloxy)pyrazolidine-1-carboxylate 9.87 g (246.6 mmol) of sodium hydride (60%) are suspended in 50 ml of DMF. 15.5 g (117.4 mmol) of tert-butylcarbazane in 100 ml of DMF are then added dropwise (considerable foaming). After stirring at RT for 2 h, 39.0 g (117.5 mmol) of step 1 are added dropwise, and the mixture is stirred at RT for 18 h. Conventional work-up gives 30.2 g (Y=85%) of step 2 as brown crude oil, which is employed directly in step 3.

Step 3 tert-Butyl 4-(tert-butyldimethylsilanyloxy)-2-(4-chlorophenylcarbamoyl)-pyrazolidine-1-carboxylate 30.1 g (99.8 mmol) of step 2 are dissolved in 200 ml of DCM, and 15.3 g (99.8 mmol) of 4-chlorophenyl isocyanate are added, and the mixture is stirred at RT for 5 h. The crude product is washed with water, dried over sodium sulfate, the solid is filtered off, and the mixture is evaporated to dryness. Chromatography on silica gel with PE/EA=8/2 gives 23.4 g of step 3 (Y=51%).

Step 4

N-(4-Chlorophenyl)-4-(tert-butyldimethylsilanyloxy) pyrazolidine-1-carboxamide 25.0 ml (13.0 mmol) of trifluoroacetic acid are added dropwise to a solution of 10.2 g (22.4 mmol) of step 3 in 50 ml of DCM, and the mixture is stirred at RT for 1 h. Conventional work-up gives 7.8 g (98%) of step 4; MS (FAB) m/e=356/358 (M+H)+.

Step 5

1-N-[(4-Chlorophenyl)]-2-N-{[4-(2-oxo-2H-pyridin-1-yl)phenyl]}-4-(tert-butyldimethylsilanyloxy)pyrazolidine-1,2-dicarboxamide 145.3 mg (0.68 mmol) of 1-(4-aminophenyl)-2H-pyridin-2-one are dissolved in 2 ml of DCM, 157.2 mg (0.78 mmol) of 4-nitrophenyl chloroformate and 62.96 µl (0.78 mmol) of pyridine are subsequently added successively, and the mixture is stirred at RT for 1 h. 277.6 mg (0.78 mmol) of step 4, 0.4 ml (2.3 mmol) of N-ethyldiisopropylamine and 2 ml of THF are added to this reaction mixture. After stirring at RT for 18 h, the mixture is subjected to conventional work-up, giving 330 mg (Y=74.5%) of step 5; MS (FAB) m/e=568/570 (M+H)+.

Step 6

"B1":

330 mg (0.58 mmol) of step 5 are dissolved in 4.0 ml of THF, and 250.0 mg (0.8 mmol) of tetra-n-butylammonium fluoride are added at RT with stirring, and stirring is subsequently continued at this temperature for 1 h. The mixture is diluted with water, and 1N HCl solution is added. The deposited precipitate is filtered off with suction, washed with water and dried, giving 190 mg (Y=72%) of "B1" as crystals; MS (FAB) m/e=454/456 (M+H)$^+$.

The following compounds are obtained analogously

1-N-[(4-chlorophenyl)]-2-N-{[4-(3-oxomorpholin-4-yl) phenyl]}-4-hydroxypyrazolidine-1,2-dicarboxamide, M+H$^+$ 460, 462;

1-N-[(4-chlorophenyl)]-2-N-{[4-(2-oxopiperidin-1-yl)phenyl]}-4-hydroxypyrazolidine-1,2-dicarboxamide, M+H$^+$ 458, 460;

1-N-[(4-chlorophenyl)]-2-N-{[3-methyl-4-(3-oxomorpholin-4-yl)-phenyl]}-4-hydroxypyrazolidine-1,2-dicarboxamide, M+H$^+$ 474, 476;

1-N-[(4-chlorophenyl)]-2-N-{[3-methyl-4-(2-oxopyrrolidinyl)phenyl]}-4-hydroxypyrazolidine-1,2-dicarboxamide, M+H$^+$ 458, 460;

1-N-[(4-chlorophenyl)]-2-N-{[3-fluoro-4-(3-oxomorpholin-4-yl)phenyl]}-4-hydroxypyrazolidine-1,2-dicarboxamide, M+H$^+$ 478, 480;

1-N-[(4-chlorophenyl)]-2-N-{[3-chloro-4-(3-oxomorpholin-4-yl)phenyl]}-4-hydroxypyrazolidine-1,2-dicarboxamide, M+H$^+$ 494, 496;

1-N-[(4-chlorophenyl)]-2-N-{[3-fluoro-4-(2-oxopyrrolidinyl)phenyl]}-4-hydroxypyrazolidine-1,2-dicarboxamide, M+H$^+$ 478, 480;

1-N-[(4-chlorophenyl)]-2-N-{[3-chloro-4-(2-oxo-2H-pyridin-1-yl)-phenyl]}-4-hydroxypyrazolidine-1,2-dicarboxamide, M+H$^+$ 488, 490;

1-N-[(4-chlorophenyl)]-2-N-{[4-(2-azabicyclo[2.2.2]-octan-3-on-2-yl)-phenyl]}-4-hydroxypyrazolidine-1,2-dicarboxamide, M+H$^+$ 488, 486;

1-N-[(4-chlorophenyl)]-2-N-{[3-trifluoromethyl-4-(2-azabicyclo[2.2.2]-octan-3-on-2-yl)phenyl]}-4-hydroxypyrazolidine-1,2-dicarboxamide, M+H$^+$ 552, 553;

1-N-[(4-chlorophenyl)]-2-N-{[3-chloro-4-(2-azabicyclo[2.2.2]-octan-3-on-2-yl)phenyl]}-4-hydroxypyrazolidine-1,2-dicarboxamide, M+H$^+$ 518, 520;

1-N-[(4-ethynylphenyl)]-2-N-{[3-chloro-4-(3-oxomorpholin-4-yl)-phenyl]}-4-hydroxypyrazolidine-1,2-dicarboxamide, 1-N-[(4-ethynylphenyl)]-2-N-{[4-(2-oxo-2H-pyridin-1-yl) phenyl]}-4-hydroxypyrazolidine-1,2-dicarboxamide, 1-N-[(4-ethynylphenyl)]-2-N-{[3-methyl-4-(3-oxomorpholin-4-yl)-phenyl]}-4-hydroxypyrazolidine-1,2-dicarboxamide, 1-N-[(4-ethynylphenyl)]-2-N-{[3-chloro-4-(3-oxomorpholin-4-yl)-phenyl]}-(R)-4-hydroxypyrazolidine-1,2-dicarboxamide, 1-N-[(4-ethynylphenyl)]-2-N-{[4-(2-oxo-2H-pyridin-1-yl) phenyl]}-(R)-4-hydroxypyrazolidine-1,2-dicarboxamide, 1-N-[(4-ethynylphenyl)]-2-N-{[3-methyl-4-(3-oxomorpholin-4-yl)-phenyl]}-(R)-4-hydroxypyrazolidine-1,2-dicarboxamide, 1-N-[(4-ethynylphenyl)]-2-N-{[3-chloro-4-(3-oxomorpholin-4-yl)-phenyl]}-(S)-4-hydroxypyrazolidine-1,2-dicarboxamide, 1-N-[(4-ethynylphenyl)]-2-N-{[4-(2-oxo-2H-pyridin-1-yl) phenyl]}-(S)-4-hydroxypyrazolidine-1,2-dicarboxamide, 1-N-[(4-ethynylphenyl)]-2-N-{[3-methyl-4-(3-oxomorpholin-4-yl)-phenyl]}-(S)-4-hydroxypyrazolidine-1,2-dicarboxamide, 1-N-[(4-bromophenyl)]-2-N-{[4-(2-oxo-2H-pyridin-1-yl) phenyl]}-4-hydroxypyrazolidine-1,2-dicarboxamide, 1-N-[(4-bromophenyl)]-2-N-{[4-(2-oxo-2H-pyridin-1-yl) phenyl]}-(S)-4-hydroxypyrazolidine-1,2-dicarboxamide, 1-N-[(4-bromophenyl)]-2-N-{[4-(2-oxo-2H-pyridin-1-yl) phenyl]}-(R)-4-hydroxypyrazolidine-1,2-dicarboxamide.

EXAMPLE 3

Reaction of 1 equivalent of the hydroxyl compounds mentioned below

1-N-[(4-ethynylphenyl)]-2-N-{[3-chloro-4-(3-oxomorpholin-4-yl)-phenyl]}-4-hydroxypyrazolidine-1,2-dicarboxamide, 1-N-[(4-ethynylphenyl)]-2-N-{[4-(2-oxo-2H-pyridin-1-yl) phenyl]}-4-hydroxypyrazolidine-1,2-dicarboxamide, 1-N-[(4-ethynylphenyl)]-2-N-{[3-methyl-4-(3-oxomorpholin-4-yl)-phenyl]}-4-hydroxypyrazolidine-1,2-dicarboxamide, 1-N-[(4-ethynylphenyl)]-2-N-{[3-chloro-4-(3-oxomorpholin-4-yl)-phenyl]}-4-hydroxypyrazolidine-1,2-dicarboxamide, 1-N-[(4-ethynylphenyl)]-2-N-{[4-(2-oxo-2H-pyridin-1-yl) phenyl]}-4-hydroxypyrazolidine-1,2-dicarboxamide, 1-N-[(4-ethynylphenyl)]-2-N-{[3-methyl-4-(3-oxomorpholin-4-yl)-phenyl]}-4-hydroxypyrazolidine-1,2-dicarboxamide, 1-N-[(4-ethynylphenyl)]-2-N-{[3-chloro-4-(3-oxomorpholin-4-yl)-phenyl]}-4-hydroxypyrazolidine-1,2-dicarboxamide, 1-N-[(4-ethynylphenyl)]-2-N-{[4-(2-oxo-2H-pyridin-1-yl) phenyl]}-4-hydroxypyrazolidine-1,2-dicarboxamide, 1-N-[(4-ethynylphenyl)]-2-N-{[3-methyl-4-(3-oxomorpholin-4-yl)-phenyl]}-4-hydroxypyrazolidine-1,2-dicarboxamide, with 1.1-1.5 equivalents of the desired acid chlorides in DCM at room temperature gives, after conventional work-up, the following compounds 1-N-[(4-ethynylphenyl)]-2-N-{[3-chloro-4-(3-oxomorpholin-4-yl)-phenyl]}-4-acetoxypyrazolidine-1,2-dicarboxamide, 1-N-[(4-ethynylphenyl)]-2-N-{[4-(2-oxo-2H-pyridin-1-yl) phenyl]}-4-benzylcarbonyloxypyrazolidine-1,2-dicarboxamide, 1-N-[(4-ethynylphenyl)]-2-N-{[3-methyl-4-(3-oxomorpholin-4-yl)-phenyl]}-4-benzoyloxypyrazolidine-1,2-dicarboxamide, 1-N-[(4-ethynylphenyl)]-2-N-{[3-chloro-4-(3-oxomorpholin-4-yl)-phenyl]}-4-tert-butylcarbonyloxypyrazolidine-1,2-dicarboxamide, 1-N-[(4-ethynylphenyl)]-2-N-{[4-(2-oxo-2H-pyridin-1-yl) phenyl]}-4-iso-butylcarbonyloxypyrazolidine-1,2-dicarboxamide, 1-N-[(4-ethynylphenyl)]-2-N-{[3-methyl-4-(3-oxomorpholin-4-yl)-phenyl]}-4-cyclohexylmethylcarbonyloxypyrazolidine-1,2-dicarboxamide, 1-N-[(4-ethynylphenyl)]-2-N-{[3-chloro-4-(3-oxomorpholin-4-yl)-phenyl]}-4-cyclopentylcarbonyloxypyrazolidine-1,2-dicarboxamide, 1-N-[(4-ethynylphenyl)]-2-N-{[4-(2-oxo-2H-pyridin-1-yl) phenyl]}-4-cyclopropylmethylcarbonyloxypyrazolidine-1,2-dicarboxamide, 1-N-[(4-ethynylphenyl)]-2-N-{[3-methyl-4-(3-oxomorpholin-4-yl)-phenyl]}-4-cyclobutylcarbonyloxypyrazolidine-1,2-dicarboxamide.

14. EXAMPLES OF THE PREPARATION OF INTERMEDIATE COMPOUNDS 14.1 All Compounds of the Following Formula VI (where R=H or methyl; n=3, 4 or 5) can be Synthesised in Accordance with the Following Scheme

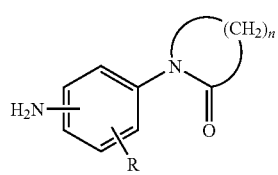

For example synthesis of 1-(4-amino-2-methylphenyl)piperidin-2-one:

14.2 Synthesis of the phenylpiperidone Unit Without a methyl Group

The preparation of 1-(4-amino-2-methylphenyl)piperidin-2-one is carried out, for example, as indicated below:

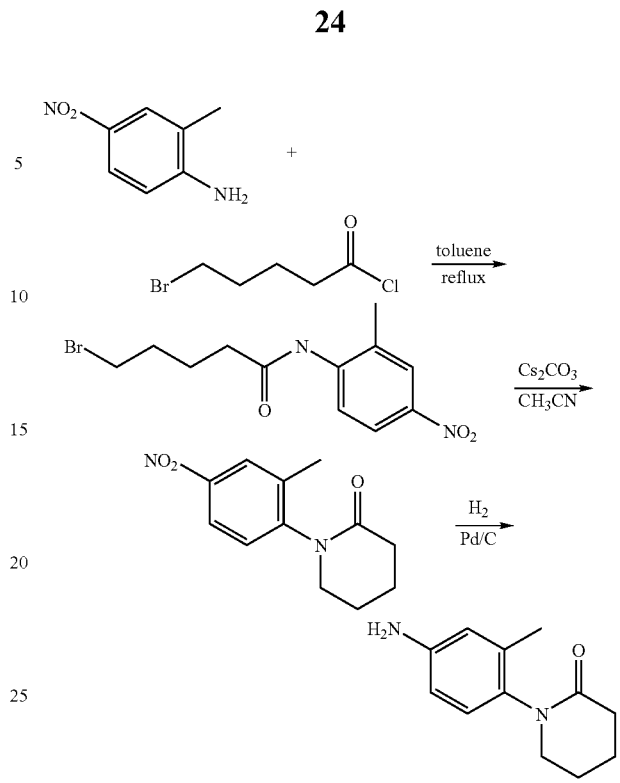

14.3 1-(4-Aminophenyl)-1H-pyrazin-2-one 14.4 1-(4-Amino-2,5-dimethylphenyl)-piperidin-2-one

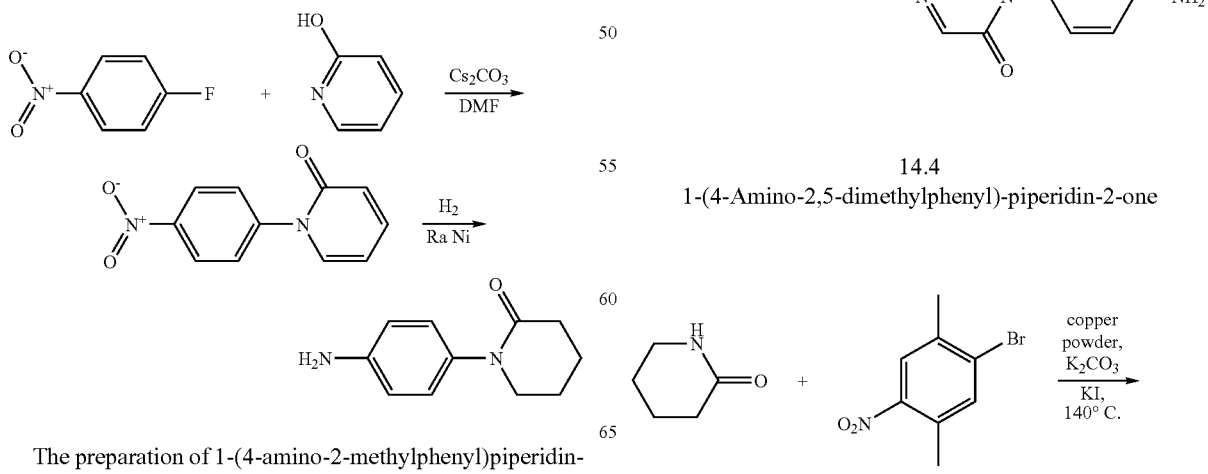

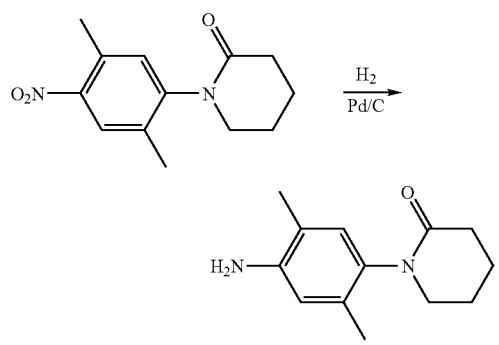
14.5 1-(4-Amino-3-methylphenyl)piperidin-2-one
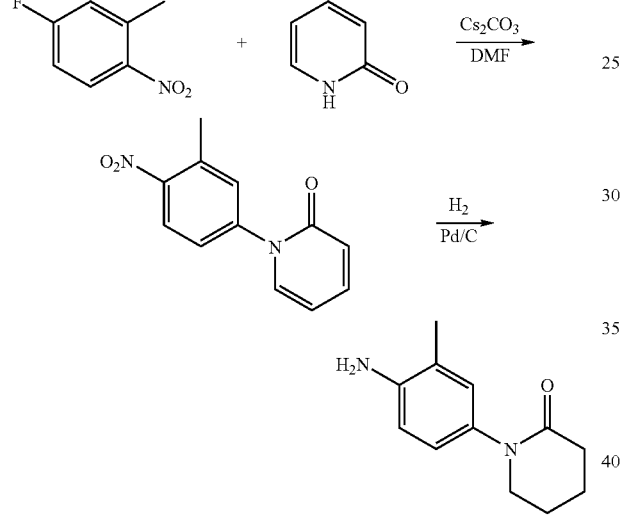
14.6 1-(5-Aminopyridin-2-yl)piperidin-2-one
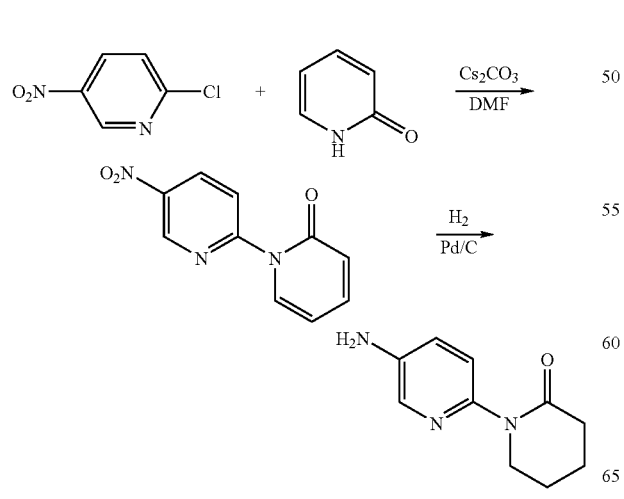
14.7 1-(4-Aminomethylphenyl)piperidin-2-one
14.8 2-(4-Aminophenyl)-2-azabicyclo[2.2.2]octan-3-one
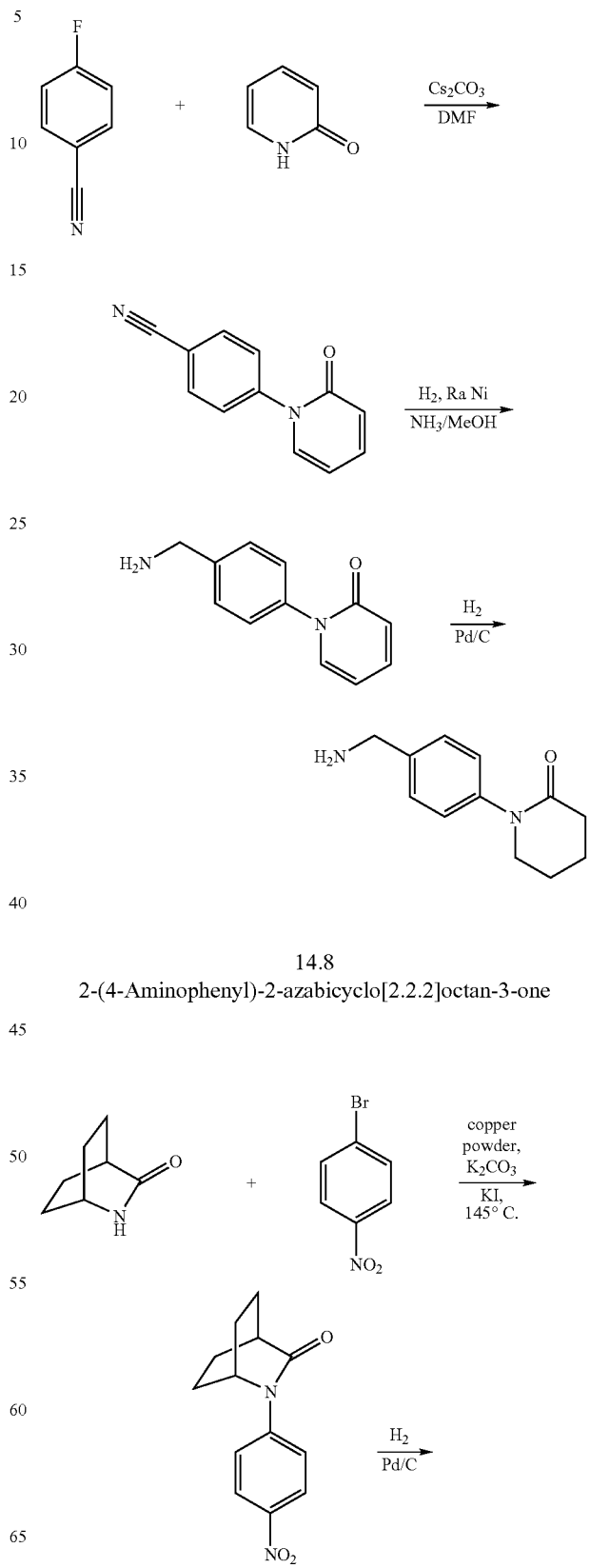

-continued
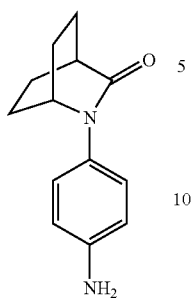
14.9 1-(3-Amino-6-ethylphenyl)pyrrolidin-2-one
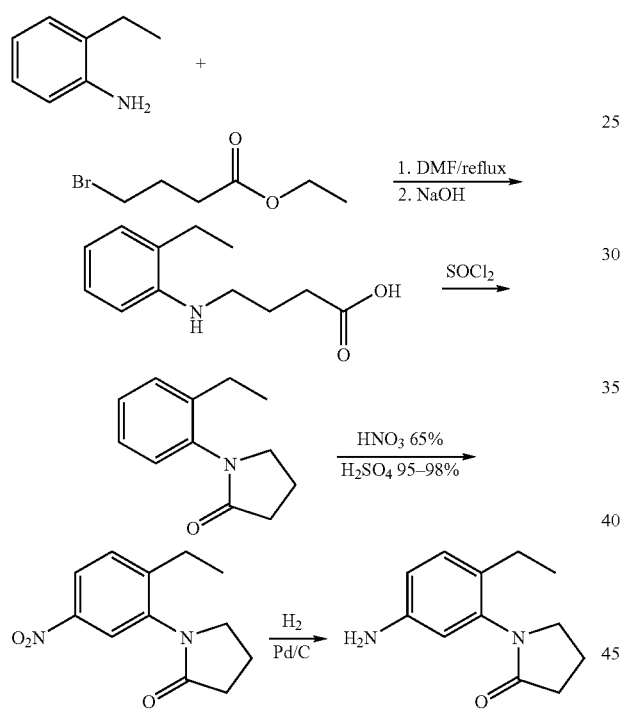
14.10 2-(4-Amino-2-trifluoromethylphenyl)-2-azabicyclo[2.2.2]octan-3-one
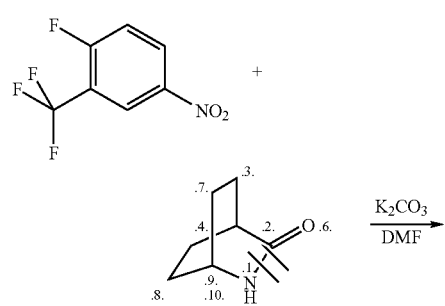
-continued
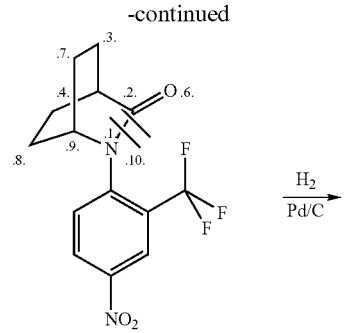
14.11 1-(4-Amino-3-chlorophenyl)pyrrolidin-2-one
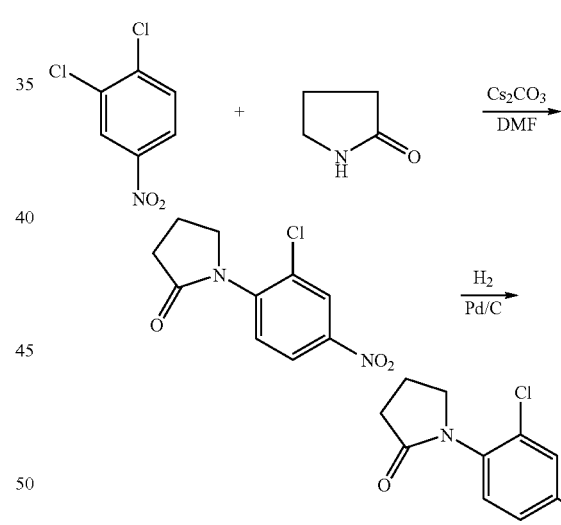
14.12 1-(4-Amino-2-trifluoromethylphenyl)piperidin-2-one
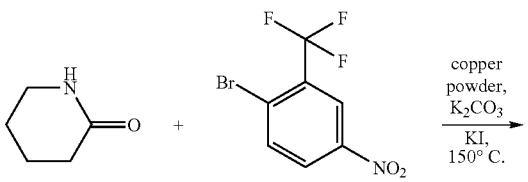

-continued
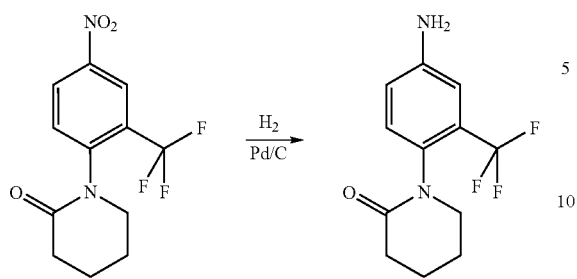
14.13 3-(4-Amino-2-methylphenyl)-1,3-oxazinan-2-one
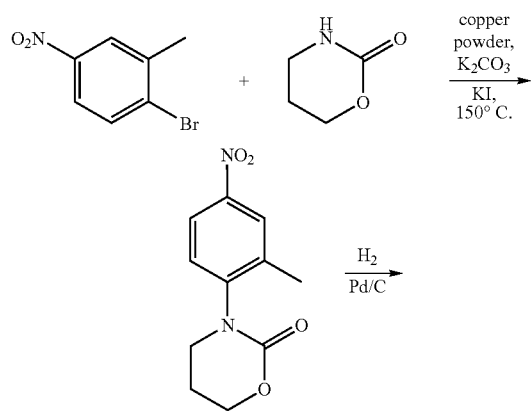
14.14 4-(4-Aminophenyl)morpholin-3-one
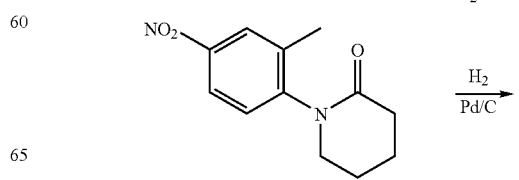
-continued
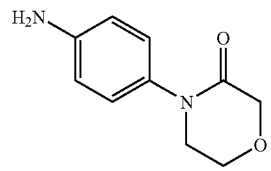
14.15 1-(4-Aminophenyl)pyridin-2-one
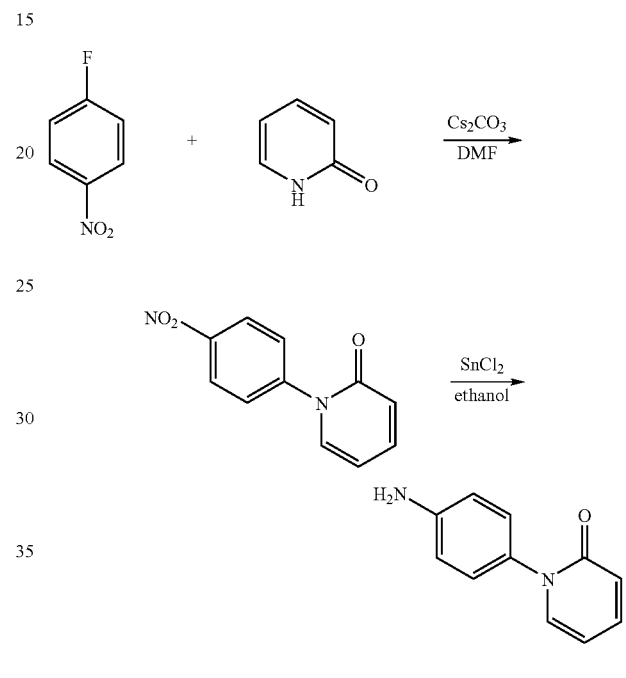
14.16 1-(4-Amino-2-methylphenyl)piperidin-2-one
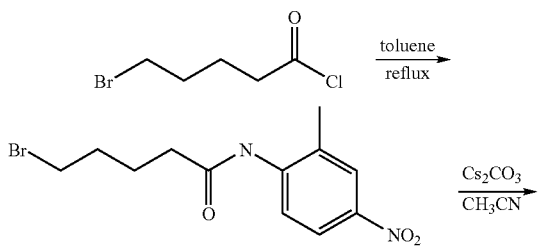

14.17 1-(4-Aminophenyl)-1H-pyridin-4-one
14.18 1-(4-Aminophenyl)4-tert-butyloxycarbonylpiperazin-2-one
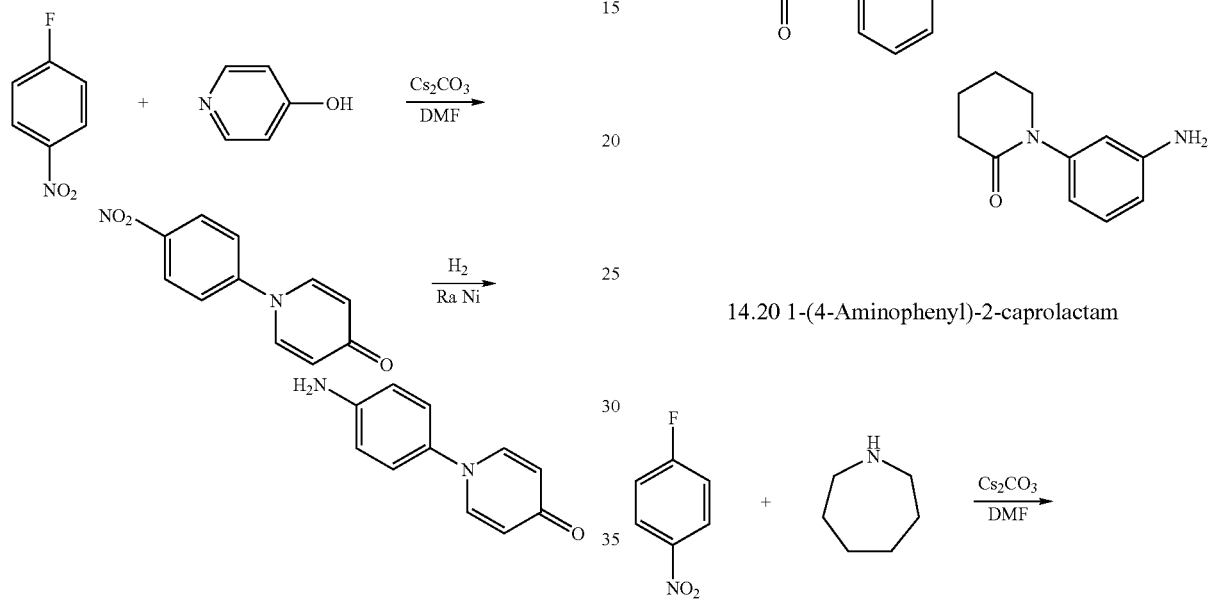
14.19 1-(3-Aminophenyl)piperidin-2-one
14.20 1-(4-Aminophenyl)-2-caprolactam
14.21 1-(4-Amino-3-fluorophenyl)piperidin-2-one
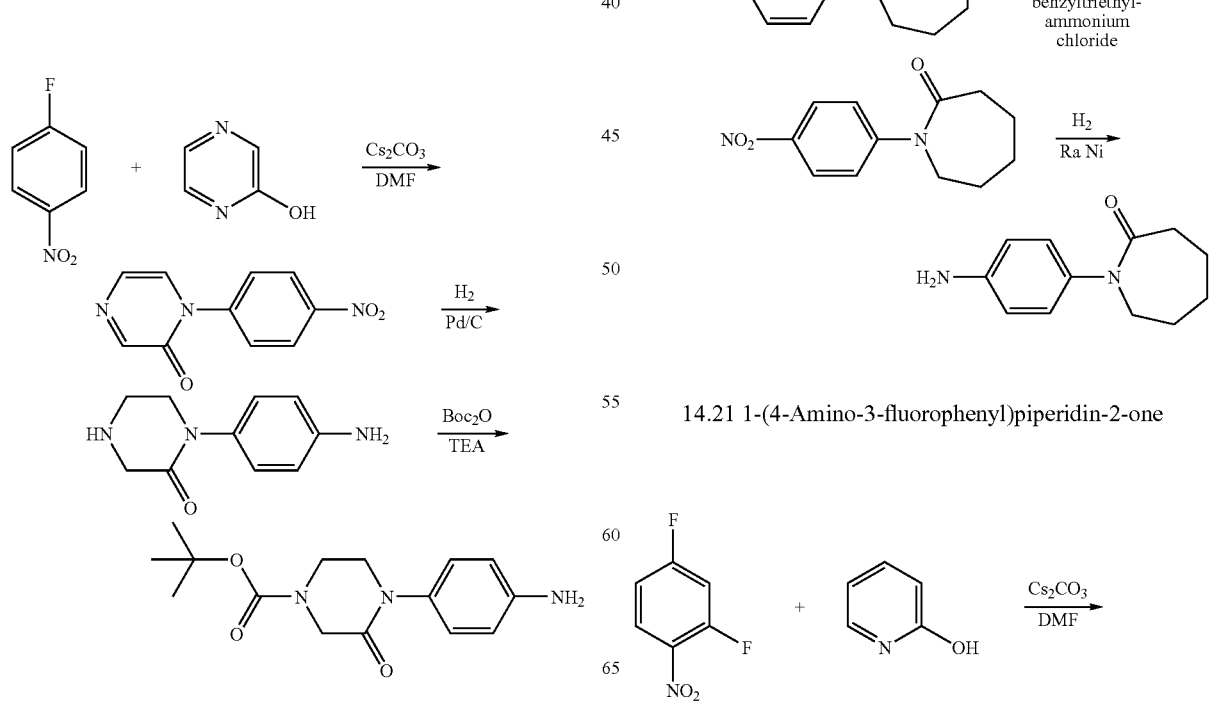

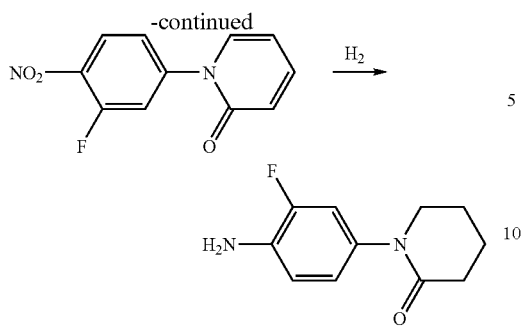

14.22 1-(4-Amino-2-fluorophenyl)piperidin-2-one

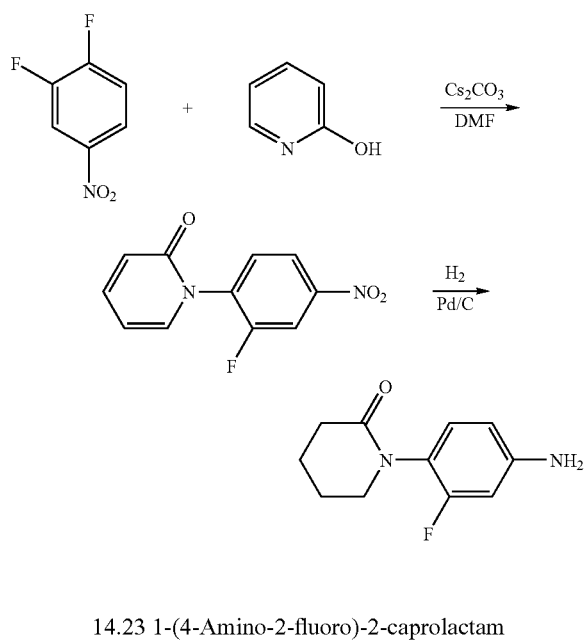

14.23 1-(4-Amino-2-fluoro)-2-caprolactam

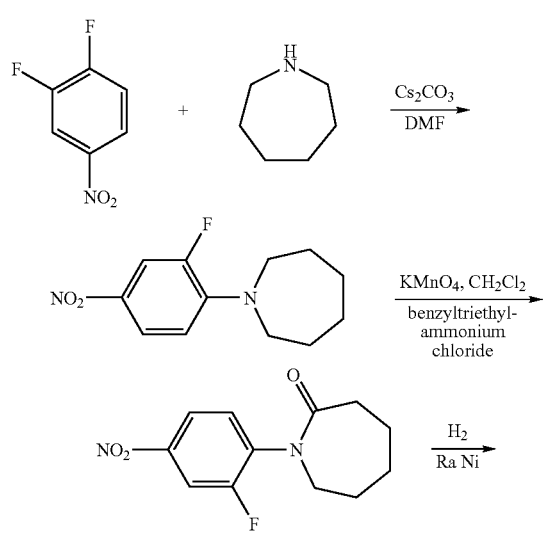

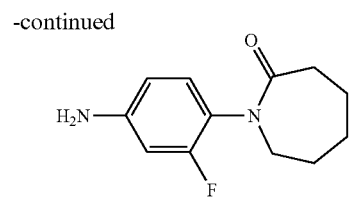

Pharmacological Data

Affinity to Receptors

TABLE 1

| Compound No. | FXa-IC$_{50}$[nM] | TF/FVIIa-IC$_{50}$[M] |
|---|---|---|
| "A1" | 75.0 | 160.0 |
| "A2" | 120.0 | 250.0 |
| "A3" | 55.0 | 120.0 |

The following examples relate to pharmaceutical compositions:

EXAMPLE A

Injection Vials

A solution of 100 g of an active ingredient of the formula I and 5 g of disodium hydrogenphosphate in 3 l of bidistilled water is adjusted to pH 6.5 using 2N hydrochloric acid, sterile filtered, transferred into injection vials, lyophilised under sterile conditions and sealed under sterile conditions. Each injection vial contains 5 mg of active ingredient.

EXAMPLE B

Suppositories

A mixture of 20 g of an active ingredient of the formula I is melted with 100 g of soya lecithin and 1400 g of cocoa butter, poured into moulds and allowed to cool. Each suppository contains 20 mg of active ingredient.

EXAMPLE C

Solution

A solution is prepared from 1 g of an active ingredient of the formula I, 9.38 g of NaH$_2$PO$_4$.2H$_2$O, 28.48 g of Na$_2$HPO$_4$.12 H$_2$O and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active ingredient of the formula I are mixed with 99.5 g of Vaseline under aseptic conditions.

EXAMPLE E

Tablets

A mixture of 1 kg of active ingredient of the formula I, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

EXAMPLE F

Coated Tablets

Tablets are pressed analogously to Example E and subsequently coated in a conventional manner with a coating of sucrose, potato starch, talc, tragacanth and dye.

EXAMPLE G

Capsules 2 kg of active ingredient of the formula I are introduced into hard gelatine capsules in a conventional manner in such a way that each capsule contains 20 mg of the active ingredient.

EXAMPLE H

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

The invention claimed is:

1. A compound of formula I

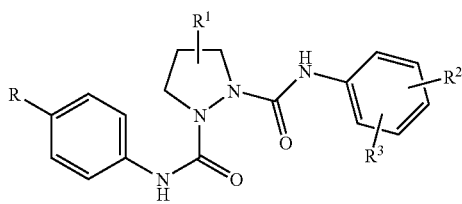

wherein

R is H, A, A—CO—, Hal, —C≡C—H, —C≡C—A, or —C≡C—C(=O)—A, $R^1$ is H, =O, Hal, A, OH, OA, A—COO—, Ph—$(CH_2)_n$—COO—, cycloalkyl-$(CH_2)_n$—COO—, A—CONH—, A—CONA—, Ph—CONA—, $N_3$, $NH_2$, $NO_2$, CN, COOH, COOA, $CONH_2$, CONHA, CON$(A)_2$, O-allyl, O-propargyl, O-benzyl, =N—OH, =N—OA, or =$CF_2$, Ph is phenyl which is unsubstituted or mono-, di- or trisubstituted by A, OA, or Hal, $R^2$ is H, Hal, or A, $R^3$ is a monocyclic saturated, unsaturated or aromatic heterocycle having 1 to 4 N, O and/or S atoms, which is unsubstituted or mono-, di- or trisubstituted by Hal, A, OA, CN, $(CH_2)_n$OH, $(CH_2)_n$Hal, $NR^4R^5$, =NH, =N—OH, =N—OA, and/or carbonyl oxygen (=O), or $CONR^4R^5$, $R^4$, $R^5$, independently of one another, are H or A, $R^4$ and $R^5$ together may also be an alkylene chain having 3, 4 or 5 C atoms, which is optionally substituted by A, Hal, OA, and/or carbonyl oxygen (=CO), A is unbranched, branched or cyclic alkyl having 1-10 C atoms, in which 1-7H atoms are each optionally replaced by F or chlorine, Hal is F, Cl, Br or I, n is 0, 1, 2, 3 or 4, or a pharmaceutically usable salt or stereoisomer thereof, including mixtures thereof in all ratios.

2. A compound according to claim 1, wherein R is Hal or —C≡C—H.

3. A compound according to claim 1, wherein $R^3$ is $CONR^4R^5$ or a monocyclic saturated, unsaturated or aromatic heterocycle having 1 to 4 N, O and/or S atoms, which is unsubstituted or mono-, di- or trisubstituted by Hal, A, OA, =NH, and/or carbonyl oxygen (=O), and $R^4$ and $R^5$ independently of one another, are each H or A, or $R^4$ and $R^5$ together are an alkylene chain having 3, 4 or 5 C atoms.

4. A compound according to claim 1, wherein $R^3$ is 2-oxopiperidin-1-yl, 2-oxopyrrolidin-1-yl, 2-oxo-1H-pyridin-1-yl, 3-oxomorpholin-4-yl, 4-oxo-1H-pyridin-1-yl, 2-oxo-1H-pyrazin-1-yl, 2-oxoimidazolidin-1-yl, 2-iminopiperidin-1-yl, 2-iminopyrrolidin-1-yl, 3-iminomorpholin-4-yl, 2-iminoimidazolidin-1-yl, 2-imino-1H-pyrazin-1-yl, 2,6-dioxopiperidin1-yl, 2-oxopiperazin-1-yl, 2,6-dioxopiperazin-1-yl, 2,5-dioxopyrrolidin-1-yl, 2-oxo-1,3-oxazolidin-3-yl, 3-oxo-2H-pyridazin-2-yl, 2-caprolactam-1-yl (=2-oxoazepan-1-yl), 2-azabicyclo[2.2.2]octan-3-on-2-yl, 5,6-dihydro-1H-pyrimidin-2-oxo-1-yl, 2-oxo-1,3-oxazinan-3-yl, 4H-1,4-oxazin-4-yl, furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, or pyrazinyl, which in each case is optionally mono- or disubstituted by Hal and/or A, or is $CONR^4R^5$, and $R^4$, $R^5$, independently of one another, are each H or A, or $R^4$ and $R^5$ together are an alkylene chain having 3, 4 or 5 C atoms.

5. A compound according to claim 1, wherein $R^1$ is H, =O, OH, OA, A—COO—, Ph—$(CH_2)_n$—COO—, or cycloalkyl-$(CH_2)_n$—COO—, and Ph is unsubstituted phenyl.

6. A compound according to claim 1, wherein

R is Hal or —C≡C—H, $R^1$ is H, =O, OH, OA, A—COO—, Ph—$(CH_2)_n$—COO—, or cycloalkyl-$(CH_2)_n$—COO—, Ph is unsubstituted phenyl, $R^2$ is H, Hal or A, $R^3$ is 2-oxopiperidin-1-yl, 2-oxopyrrolidin-1-yl, 2-oxo-1H-pyridin-1-yl, 3-oxomorpholin-4-yl, 4-oxo-1H-pyridin-1-yl, 2-oxo-1H-pyrazin-1-yl, 2-oxoimidazolidin-1-yl, 2-iminopiperidin-1-yl, 2-iminopyrrolidin-1-yl, 3-iminomorpholin-4-yl, 2-iminoimidazolidin-1-yl, 2-imino-1H-pyrazin-1-yl, 2,6-dioxopiperidin1-yl, 2-oxopiperazin-1-yl, 2,6-dioxopiperazin-1-yl, 2,5-dioxopyrrolidin-1-yl, 2-oxo-1,3-oxazolidin-3-yl, 3-oxo-2H-pyridazin-2-yl, 2-caprolactam-1-yl (=2-oxoazepan-1-yl), 2-azabicyclo[2.2.2]octan-3-on-2-yl, 5,6-dihydro-1H-pyrimidin-2-oxo-1-yl, 2-oxo-1,3-oxazinan-3-yl, 4H-1,4-oxazin-4-yl, furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, or pyrazinyl, which in each case is optionally mono- or disubstituted by Hal and/or A, or is $CONR^4R^5$, and R⁴ and R⁵ are each, independently of one another, H or A, or R⁴ and R⁵ together are an alkylene chain having 3, 4 or 5 C atoms.

7. A compound according to claim 1, wherein R³ is 2-oxopiperidin-1-yl, 2-oxopyrrolidin-1-yl, 2-oxo-1H-pyridin-1-yl, 3-oxomorpholin-4-yl, 4-oxo-1H-pyridin-1-yl, 2-oxo-1H-pyrazin-1-yl, 2-oxoimidazolidin-1-yl, 2-iminopiperidin-1-yl, 2-iminopyrrolidin-1-yl, 3-iminomorpholin-4-yl, 2-iminoimidazolidin-1-yl, 2-imino-1H-pyrazin-1-yl, 2,6-dioxopiperidin1-yl, 2-oxopiperazin-1-yl, 2,6-dioxopiperazin-1-yl, 2,5-dioxopyrrolidin-1-yl, 2-oxo-1,3-oxazolidin-3-yl, 3-oxo-2H-pyridazin-2-yl, 2-caprolactam-1-yl (=2-oxoazepan-1-yl), 2-azabicyclo[2.2.2]-octan-3-on-2-yl, 5,6-dihydro-1H-pyrimidin-2-oxo-1-yl, 2-oxo-1,3-oxazinan-3-yl, or 4H-1,4-oxazin-4-yl, which in each case is optionally mono- or disubstituted by Hal and/or A.

8. A compound according to claim 1, wherein R³ is 2-oxopiperidin-1-yl, 2-oxopyrrolidin-1-yl, 2-oxo-1H-pyridin-1-yl, 3-oxomorpholin-4-yl, 4-oxo-1H-pyridin-1-yl, 2-oxo-1H-pyrazin-1-yl, 2-oxoimidazolidin-1-yl, 2,6-dioxopiperidin1-yl, 2-oxopiperazin-1-yl, 2,6-dioxopiperazin-1-yl, 2,5-dioxopyrrolidin-1-yl, 2-oxo-1,3-oxazolidin-3-yl, 3-oxo-2H-pyridazin-2-yl, 2-caprolactam-1-yl (=2-oxoazepan-1-yl), 2-azabicyclo[2.2.2]-octan-3-on-2-yl, 5,6-dihydro-1H-pyrimidin-2-oxo-1-yl, 2-oxo-1,3-oxazinan-3-yl, or 4H-1,4-oxazin-4-yl.

9. A compound according to claim 1, wherein
R is Hal or —C≡C—H,
R¹ is H, =O, OH, OA, A—COO—, Ph—(CH₂)ₙ—COO—, or cycloalkyl-(CH₂)ₙ—COO—,
Ph is unsubstituted phenyl,
R² is H, Hal or A,
R³ is 2-oxopiperidin-1-yl, 2-oxopyrrolidin-1-yl, 2-oxo-1H-pyridin-1-yl, 3-oxomorpholin-4-yl, 4-oxo-1H-pyridin-1-yl, 2-oxo-1H-pyrazin-1-yl, 2-oxoimidazolidin-1-yl, 2,6-dioxopiperidin1-yl, 2-oxopiperazin-1-yl, 2,6-dioxopiperazin-1-yl, 2,5-dioxopyrrolidin-1-yl, 2-oxo-1,3-oxazolidin-3-yl, 3-oxo-2H-pyridazin-2-yl, 2-caprolactam-1-yl (=2-oxoazepan-1-yl), 2-azabicyclo[2.2.2]-octan-3-on-2-yl, 5,6-dihydro-1H-pyrimidin-2-oxo-1-yl, 2-oxo-1,3-oxazinan-3-yl, or 4H-1,4-oxazin-4-yl,
A is unbranched, branched or cyclic alkyl having 1-10 C atoms, in which 1-7H atoms are each optionally replaced by F or chlorine,
Hal is F, Cl, Br or I, and
n is 0, 1, 2, 3 or 4.

10. A compound according to claim 1, wherein said compound is:
1-N-[(4-ethynylphenyl)]-2-N-{[3-chloro-4-(3-oxomorpholin-4-yl)phenyl]}-pyrazolidine-1,2-dicarboxamide,
1-N-[(4-chlorophenyl)]-2-N-{[3-chloro-4-(3-oxomorpholin-4-yl)phenyl]}-pyrazolidine-1,2-dicarboxamide,
1-N-[(4-chlorophenyl)]-2-N-{[4-(3-oxomorpholin-4-yl)phenyl]}-4-hydroxypyrazolidine-1,2-dicarboxamide,
1-N-[(4-chlorophenyl)]-2-N-{[4-(2-oxo-2H-pyridin-1-yl)phenyl]}-4-hydroxypyrazolidine-1,2-dicarboxamide,
1-N-[(4-chlorophenyl)]-2-N-{[4-(2-oxopiperidin-1-yl)phenyl]}-4-hydroxypyrazolidine-1,2-dicarboxamide,
1-N-[(4-chlorophenyl)]-2-N-{[3-methyl-4-(3-oxomorpholin-4-yl)phenyl]}-4-hydroxypyrazolidine-1,2-dicarboxamide,
1-N-[(4-chlorophenyl)]-2-N-{[3-methyl-4-(2-oxopyrrolidinyl)phenyl]}-4-hydroxypyrazolidine-1,2-dicarboxamide,
1-N-[(4-chlorophenyl)]-2-N-{[3-fluoro-4-(3-oxomorpholin-4-yl)phenyl]}-4-hydroxypyrazolidine-1,2-dicarboxamide,
1-N-[(4-chlorophenyl)]-2-N-{[3-chloro-4-(3-oxomorpholin-4-yl)phenyl]}-4-hydroxypyrazolidine-1,2-dicarboxamide,
1-N-[(4-chlorophenyl)]-2-N-{[3-fluoro-4-(2-oxopyrrolidinyl)phenyl]}-4-hydroxypyrazolidine-1,2-dicarboxamide,
1-N-[(4-chlorophenyl)]-2-N-{[3-chloro-4-(2-oxo-2H-pyridin-1-yl)phenyl]}-4-hydroxypyrazolidine-1,2-dicarboxamide,
1-N-[(4-chlorophenyl)]-2-N-{[4-(2-azabicyclo[2.2.2]-octan-3-on-2-yl)phenyl]}-4-hydroxypyrazolidine-1,2-dicarboxamide,
1-N-[(4-chlorophenyl)]-2-N-{[3-trifluoromethyl-4-(2-azabicyclo[2.2.2]-octan-3-on-2-yl)phenyl]}-4-hydroxypyrazolidine-1,2-dicarboxamide,
1-N-[(4-chlorophenyl)]-2-N-{[3-chloro-4-(2-azabicyclo[2.2.2]-octan-3-on-2-yl)phenyl]}-4-hydroxypyrazolidine-1,2-dicarboxamide,
1-N-[(4-chlorophenyl)]-2-N-{[4-(2-oxo-2H-pyridin-1-yl)phenyl]}pyrazolidine-1,2-dicarboxamide,
1-N-[(4-chlorophenyl)]-2-N-{[3-methyl-4-(3-oxomorpholin-4-yl)phenyl]}-pyrazolidine-1,2-dicarboxamide,
1-N-[(4-chlorophenyl)]-2-N-{[3-fluoro-4-(3-oxomorpholin-4-yl)phenyl]}-pyrazolidine-1,2-dicarboxamide,
1-N-[(4-chlorophenyl)]-2-N-{[3-chloro-4-(2-oxo-2H-pyridin-1-yl)phenyl]}-pyrazolidine-1,2-dicarboxamide,
1-N-[(4-chlorophenyl)]-2-N-{[3-chloro-4-(2-azabicyclo[2.2.2]-octan-3-on-2-yl)phenyl]}pyrazolidine-1,2-dicarboxamide,
1-N-[(4-chlorophenyl)]-2-N-{[3-methyl-4-(2-oxopyrrolidinyl)phenyl]}pyrazolidine-1,2-dicarboxamide,
1-N-[(4-chlorophenyl)]-2-N-{[4-(3-oxomorpholin-4-yl)phenyl]}-4-oxopyrazolidine-1,2-dicarboxamide,
1-N-[(4-chlorophenyl)]-2-N-{[4-(2-oxopiperidinyl)phenyl]}pyrazolidine-1,2-dicarboxamide,
1-N-[(4-chlorophenyl)]-2-N-{[4-(3-oxomorpholin-4-yl)phenyl]}pyrazolidine-1,2-dicarboxamide,
1-N-[(4-chlorophenyl)]-2-N-{[2-fluoro-4-(3-oxomorpholin-4-yl)phenyl]}-pyrazolidine-1,2-dicarboxamide,
1-N-[(4-chlorophenyl)]-2-N-{[3-trifluoromethyl-4-(2-azabicyclo[2.2.2]-octan-3-on-2-yl)phenyl]}pyrazolidine-1,2-dicarboxamide,
1-N-[(4-chlorophenyl)]-2-N-{[4-(2-azabicyclo[2.2.2]-octan-3-on-2-yl)phenyl]}-pyrazolidine-1,2-dicarboxamide,
1-N-[(4-chlorophenyl)]-2-N-{[4-(2-oxo-1,3-oxazinan-3-yl)phenyl]}pyrazolidine-1,2-dicarboxamide,
1-N-[(4-ethynylphenyl)]-2-N-{[4-(2-oxo-2H-pyridin-1-yl)phenyl]}pyrazolidine-1,2-dicarboxamide,
1-N-[(4-ethynylphenyl)]-2-N-{[3-methyl-4-(3-oxomorpholin-4-yl)phenyl]}-pyrazolidine-1,2-dicarboxamide,
1-N-[(4-ethynylphenyl)]-2-N-{[3-chloro-4-(3-oxomorpholin-4-yl)phenyl]}-4-hydroxypyrazolidine-1,2-dicarboxamide,
1-N-[(4-ethynylphenyl)]-2-N-{[4-(2-oxo-2H-pyridin-1-yl)phenyl]}-4-hydroxypyrazolidine-1,2-dicarboxamide,
1-N-[(4-ethynylphenyl)]-2-N-{[3-methyl-4-(3-oxomorpholin-4-yl)phenyl]}-4-hydroxypyrazolidine-1,2-dicarboxamide,
1-N-[(4-ethynylphenyl)]-2-N-{[3-chloro-4-(3-oxomorpholin-4-yl)phenyl]}-(R)-4-hydroxypyrazolidine-1,2-dicarboxamide, 1-N-[(4-ethynylphenyl)]-2-N-{[4-(2-oxo-2H-pyridin-1-yl)phenyl]}-(R)-4-hydroxypyrazolidine-1,2-dicarboxamide,
1-N-[(4-ethynylphenyl)]-2-N-{[3-methyl-4-(3-oxomorpholin-4-yl)phenyl]}-(R)-4-hydroxypyrazolidine-1,2-dicarboxamide,
1-N-[(4-ethynylphenyl)]-2-N-{[3-chloro-4-(3-oxomorpholin-4-yl)phenyl]}-(S)-4-hydroxypyrazolidine-1,2-dicarboxamide,
1-N-[(4-ethynylphenyl)]-2-N-{[4-(2-oxo-2H-pyridin-1-yl)phenyl]}-(S)-4-hydroxypyrazolidine-1,2-dicarboxamide,
1-N-[(4-ethynylphenyl)]-2-N-{[3-methyl-4-(3-oxomorpholin-4-yl)phenyl]}-(S)-4-hydroxypyrazolidine-1,2-dicarboxamide,
1-N-[(4-ethynylphenyl)]-2-N-{[3-chloro-4-(3-oxomorpholin-4-yl)phenyl]}-4-acetoxypyrazolidine-1,2-dicarboxamide,
1-N-[(4-ethynylphenyl)]-2-N-{[4-(2-oxo-2H-pyridin-1-yl)phenyl]}-4-benzylcarbonyloxypyrazolidine-1,2-dicarboxamide,
1-N-[(4-ethynylphenyl)]-2-N-{[3-methyl-4-(3-oxomorpholin-4-yl)phenyl]}-4-benzoyloxypyrazolidine-1,2-dicarboxamide,
1-N-[(4-ethynylphenyl)]-2-N-{[3-chloro-4-(3-oxomorpholin-4-yl)phenyl]}-4-tert-butylcarbonyloxypyrazolidine-1,2-dicarboxamide,
1-N-[(4-ethynylphenyl)]-2-N-{[4-(2-oxo-2H-pyridin-1-yl)phenyl]}-4-isobutylcarbonyloxypyrazolidine-1,2-dicarboxamide,
1-N-[(4-ethynylphenyl)]-2-N-{[3-methyl-4-(3-oxomorpholin-4-yl)phenyl]}-4-cyclohexylmethylcarbonyloxypyrazolidine-1,2-dicarboxamide,
1-N-[(4-ethynylphenyl)]-2-N-{[3-chloro-4-(3-oxomorpholin-4-yl)phenyl]}-4-cyclopentylcarbonyloxypyrazolidine-1,2-dicarboxamide,
1-N-[(4-ethynylphenyl)]-2-N-{[4-(2-oxo-2H-pyridin-1-yl)phenyl]}-4-cyclopropylmethylcarbonyloxypyrazolidine-1,2-dicarboxamide,
1-N-[(4-ethynylphenyl)]-2-N-{[3-methyl-4-(3-oxomorpholin-4-yl)phenyl]}-4-cyclobutylcarbonyloxypyrazolidine-1,2-dicarboxamide,
1-N-[(4-bromophenyl)]-2-N-{[4-(2-oxo-2H-pyridin-1-yl)phenyl]}-pyrazolidine-1,2-dicarboxamide,
1-N-[(4-bromophenyl)]-2-N-{[4-(2-oxo-2H-pyridin-1-yl)phenyl]}-4-hydroxypyrazolidine-1,2-dicarboxamide,
1-N-[(4-bromophenyl)]-2-N-{[4-(2-oxo-2H-pyridin-1-yl)phenyl]}-(S)-4-hydroxypyrazolidine-1,2-dicarboxamide,
1-N-[(4-bromophenyl)]-2-N-{[4-(2-oxo-2H-pyridin-1-yl)phenyl]}-(R)-4-hydroxypyrazolidine-1,2-dicarboxamide,
or a pharmaceutically usable salt or stereoisomers thereof, including mixtures thereof in all ratios.

11. A process for the preparation of a compound according to claim 1, said process comprising:
a) reacting a compound of formula II

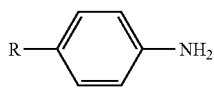

with a chloroformate derivative to give an intermediate carbamate derivative, which is subsequently reacted with a compound of formula III-1

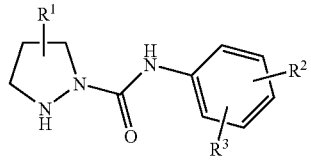

wherein if $R^1$ is OH, the OH group is optionally in protected form,
and subsequently optionally removing the OH-protecting group,
or
b) reacting a compound of the formula IV

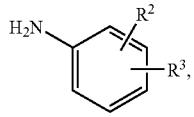

with a chloroformate derivative to give an intermediate carbamate derivative, which is subsequently reacted with a compound of formula III-2

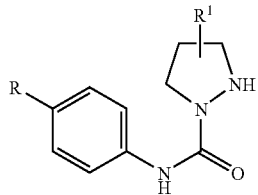

wherein if $R^1$ is H, the OH group is optionally in protected form,
and subsequently optionally removing the OH-protecting group,
and/or
(c) converting a base or acid of the formula I into one of its salts.

12. A pharmaceutical composition comprising at least one compound according to claim 1 and one or more excipients and/or adjuvants.

13. A pharmaceutical composition comprising at least one compound of the formula I according to claim 1 and at least one further medicament active ingredient.

14. A kit comprising separate packs of:
(a) an effective amount of a compound according to claim 1, and
(b) an effective amount of a further medicament active ingredient.

* * * * *